United States Patent
Ging et al.

(10) Patent No.: US 8,042,538 B2
(45) Date of Patent: Oct. 25, 2011

(54) NASAL MASK ASSEMBLY

(75) Inventors: Anthony M. Ging, Summer Hill (AU); Philip R. Kwok, Chatswood (AU); Gary C. Robinson, East Killara (AU); Bianto Santoso, Kingsgrove (AU); Rachael E. Moore, North Bondi (AU); Patrick J. McAuliffe, Chatswood (AU)

(73) Assignee: ResMed Limited, Bella Vista (AU)

( * ) Notice: Subject to any disclaimer, the term of this patent is extended or adjusted under 35 U.S.C. 154(b) by 1375 days.

(21) Appl. No.: 10/781,949

(22) Filed: Feb. 20, 2004

(65) Prior Publication Data

US 2004/0221850 A1 Nov. 11, 2004

Related U.S. Application Data

(60) Provisional application No. 60/448,533, filed on Feb. 21, 2003, provisional application No. 60/465,790, filed on Apr. 28, 2003.

(51) Int. Cl.
*A62B 18/02* (2006.01)
*A62B 18/08* (2006.01)

(52) U.S. Cl. ......... 128/206.21; 128/205.25; 128/206.12; 128/206.13; 128/206.18; 128/206.23; 128/206.24; 128/206.26; 128/206.27; 128/206.28; 128/207.11; 128/207.13

(58) Field of Classification Search ............. 128/205.25, 128/206.12, 206.13, 206.18, 206.21, 206.23, 128/206.24, 206.26, 206.27, 206.28, 207.11, 128/207.13, 201.22, 201.23, 201.29, 2.13, 128/206.188

See application file for complete search history.

(56) References Cited

U.S. PATENT DOCUMENTS

| | | | |
|---|---|---|---|
| 1,632,449 A | | 6/1927 | McKesson |
| 2,123,353 A | | 7/1938 | Catt |
| 2,245,658 A | | 6/1941 | Erickson |
| 2,254,854 A | | 9/1941 | O'Connell |
| 2,260,701 A | | 10/1941 | Boothby et al. |
| 2,834,339 A | | 5/1958 | Bennett et al. |
| 2,944,547 A | | 7/1960 | Ziherl et al. |
| 3,117,574 A | * | 1/1964 | Replogle .................. 128/206.27 |
| 3,182,659 A | | 5/1965 | Blount |
| 3,796,216 A | | 3/1974 | Schwarz |
| 3,827,433 A | | 8/1974 | Shannon |
| 3,923,054 A | | 12/1975 | Bauer, Jr. |
| 4,232,476 A | | 11/1980 | Lieberman |
| 4,406,283 A | | 9/1983 | Bir |
| 4,657,010 A | * | 4/1987 | Wright ..................... 128/205.25 |

(Continued)

FOREIGN PATENT DOCUMENTS

FR 2775905 A1 9/1999

(Continued)

OTHER PUBLICATIONS

"Comfort Flap Small Child: Contour Nasal Mask Accessory Instructions For Use", Respironics Inc., 1993, pp. 1-2.

(Continued)

*Primary Examiner* — Patricia Bianco
*Assistant Examiner* — Nihir Patel
(74) *Attorney, Agent, or Firm* — Nixon & Vanderhye P.C.

(57) ABSTRACT

A mask system is provided to fit pre-adult patients, or patients having facial features that are very small or child-like, e.g., patients having dimensions in the lower 5%-10% of the population. For example, the headgear and/or cushion are dimensioned to accommodate this range of patients.

14 Claims, 32 Drawing Sheets

U.S. PATENT DOCUMENTS

| | | | |
|---|---|---|---|
| 4,774,946 A | 10/1988 | Ackerman | |
| 4,809,692 A | 3/1989 | Nowacki et al. | |
| 4,832,015 A | 5/1989 | Nowacki | |
| 4,896,666 A | 1/1990 | Hinkle | |
| 4,944,310 A | 7/1990 | Sullivan | |
| 5,271,391 A | 12/1993 | Graves | |
| 5,318,590 A | 6/1994 | Brennan | |
| 5,462,050 A | 10/1995 | Dahlstrand | |
| 5,509,408 A | 4/1996 | Kurtis | |
| 5,535,741 A | 7/1996 | Widerstrom | |
| 5,660,174 A | 8/1997 | Jacobelli | |
| 5,813,423 A | 9/1998 | Kirchgeorg | |
| 6,000,109 A * | 12/1999 | Anscher | 24/614 |
| 6,112,746 A | 9/2000 | Kwok | |
| 6,119,693 A | 9/2000 | Kwok | |
| 6,119,694 A | 9/2000 | Correa et al. | |
| 6,357,441 B1 | 3/2002 | Kwok | |
| 6,374,826 B1 | 4/2002 | Gunaratnam | |
| 6,412,487 B1 | 7/2002 | Gunaratnam | |
| 6,412,488 B1 | 7/2002 | Barnett et al. | |
| 6,418,929 B1 * | 7/2002 | Norfleet | 128/207.11 |
| 6,439,230 B1 | 8/2002 | Gunaratnam | |
| 6,463,931 B1 | 10/2002 | Kwok | |
| 6,470,886 B1 | 10/2002 | Jestrabek-Hart | |
| D485,905 S | 1/2004 | Moore | |
| 7,007,696 B2 * | 3/2006 | Palkon et al. | 128/207.13 |
| 7,036,508 B2 | 5/2006 | Kwok | |
| 2002/0104531 A1 | 8/2002 | Malone | |
| 2002/0117177 A1 | 8/2002 | Kwok | |
| 2003/0196655 A1 | 10/2003 | Ging | |
| 2003/0196656 A1 | 10/2003 | Moore | |
| 2003/0196657 A1 | 10/2003 | Ging | |
| 2003/0196658 A1 | 10/2003 | Ging | |
| 2003/0196662 A1 | 10/2003 | Ging | |

FOREIGN PATENT DOCUMENTS

| | | |
|---|---|---|
| GB | 2277688 | 11/1994 |
| WO | WO 95/09023 | 4/1995 |
| WO | WO 99/04842 A1 | 2/1999 |
| WO | 0132250 A1 | 5/2001 |
| WO | WO 02/05883 | 1/2002 |

OTHER PUBLICATIONS

Supplementary European Search Report Mailed Jun. 29, 2009 in European Application No. 04712965.5 (5 pages).

Examination Report Mailed Oct. 5, 2009 in New Zealand Application No. 579949 (3 pages).

Examination Report Mailed May 12, 2006 in New Zealand Application No. 541912 (2 pages).

Examination Report Mailed Apr. 7, 2008 in New Zealand Application No. 567066 (2 pages).

Examination Report Mailed Mar. 16, 2011 in New Zealand Application No. 591697 (3 pages).

Notice of Reasons for Rejection Mailed Sep. 1, 2009 in Japanese Application No. 2006-501368, with English Translation (8 pages).

Decision of Rejection Mailed Jun. 1, 2010 in Japanese Application No. 2006-501368, with English translation (4 pages).

Notification of the First Office Action Mailed Feb. 15, 2008 in Chinese Application No. 200480004798.1 (7 pages).

Notification of the Second Office Action Mailed Aug. 29, 2008 in Chinese Application No. 200480004798.1 (10 pages).

Notification of the Third Office Action Mailed Apr. 3, 2009 in Chinese Application No. 200480004798.1 (6 pages).

Examiner's First Report Mailed Mar. 9, 2009 in Australian Application No. 2004212632 (3 pages).

* cited by examiner

Vista™ ............
Kidsta Small -----------
Kid ———————

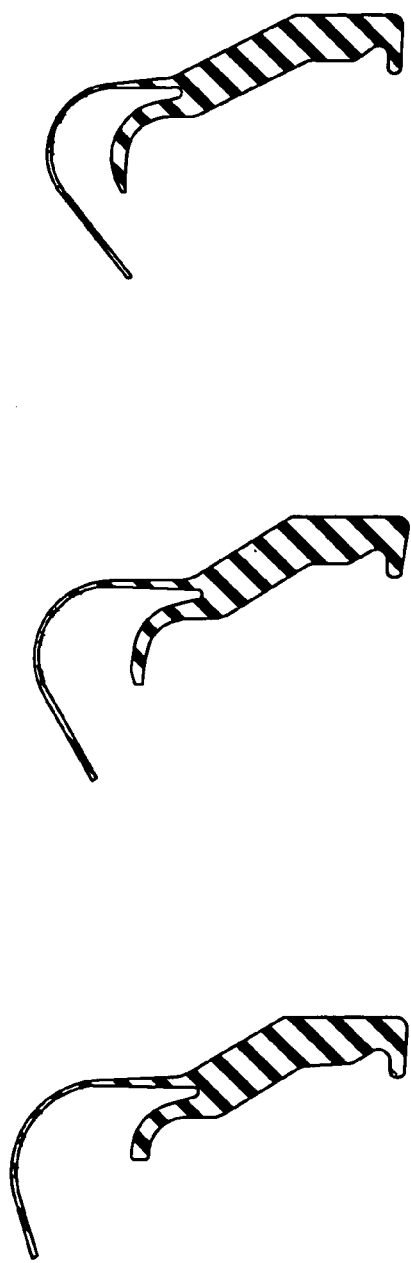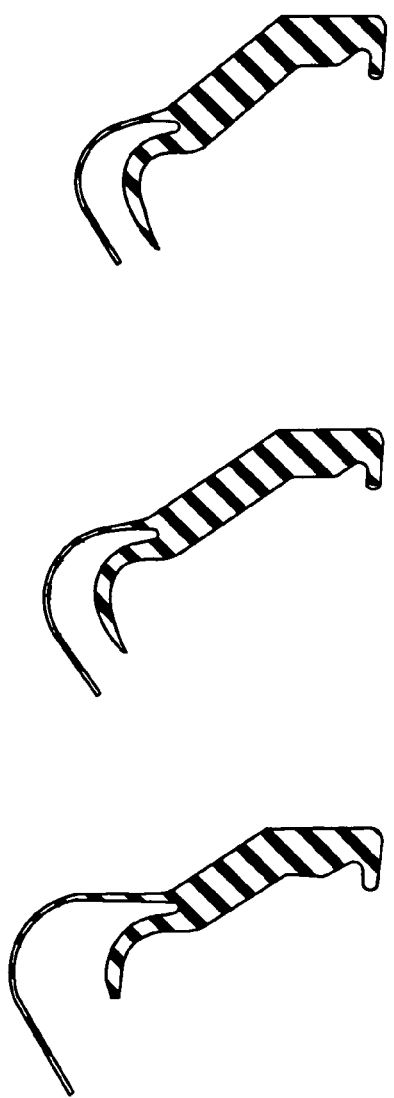

NASAL MASK ASSEMBLY

CROSS REFERENCE TO PRIORITY APPLICATIONS

The present application claims the benefit of U.S. Provisional Patent Application No. 60/448,533 filed Feb. 21, 2003 and 60/465,790 filed Apr. 28, 2003, each of which is incorporated herein by reference in its entirety.

BACKGROUND OF THE INVENTION

1. Field of the Invention

The invention relates to a nasal mask assembly for use with non-invasive positive pressure ventilation (NIPPV) applied to small adults or pre-adults with sleep disordered breathing (SDB).

2. Description of Related Art

Sleep-disordered breathing is a general term for a sleep disorder with apneas and hypopneas. Apneas are generally taken to be a cessation of airflow for ten seconds or longer. Hypopnea are generally taken to be a 50% or greater decrease in air flow for ten seconds or longer. Both apneas and hypopneas cause sleep arousals—moments when an individual wakes enough to resume breathing but not enough to remember any interruption of sleep. Some arousals simply cause the sleeper to shift into a lighter stage of sleep. In either case, the arousal lessens the quality of sleep. Apneas and hypopneas may cause blood oxygen levels to drop. Apneas and hypopneas result from upper airway obstruction, either full or partial, or a dysfunction of the body's automatic drive to breathe.

Obstructive Sleep Apnea (OSA) is a common disorder. Estimates for the number of Americans with OSA vary depending on the criteria researchers use for the study. Conservative estimates, however, put the number of adult Americans with OSA at approximately 20 million. OSA occurs because of upper airway obstructions that can cause you to snore or to stop breathing. Obstructions occur during sleep for two primary reasons: lack of muscle tone and/or gravity. Excess tissue in the upper airway and anatomic abnormalities compound these factors. During sleep, especially in REM sleep, our bodies relax, and muscle tissues like the tongue and soft palate lose their slight rigidity. Because we tend to sleep lying down, gravity pulls these tissues toward the back of the throat and closes the upper airway.

The use of nasal Continuous Positive Airway Pressure (nasal CPAP) to treat obstructive sleep apnea (OSA) was taught by Sullivan in U.S. Pat. No. 4,944,310. Today apparatus for OSA typically comprises (i) a blower which provides a supply of air or breathable gas at positive pressure, (ii) an air delivery conduit connected to the blower, and (iii) a patient interface, such as a nasal mask, which is connected to the air delivery conduit.

A variety of nasal masks have been developed. One such mask is the MIRAGE® mask, manufactured by ResMed Limited and described in U.S. Pat. Nos. 6,112,746; 6,357,441; 6,119,693 and 6,463,931, amongst others. Another such mask is the ULTRA MIRAGE® mask, also manufactured by ResMed Limited. The ULTRA MIRAGE® mask is described in U.S. Pat. Nos. 6,112,746, 6,357,441, 6,374,826, 6,412,487, 6,439,230 and 6,463,931.

The American Academy of Pediatrics, in a Technical Report on the Diagnosis and Management of Childhood Obstructive Sleep Apnea Syndrome (OSAS) (PEDIATRICS Vol. 109 No. 4 April 2002.) noted that "Snoring is a common occurrence in childhood, with reported prevalence between 3.2% and 12.1%. The prevalence of childhood OSAS is difficult to estimate, largely because published studies use different PSG criteria for its ascertainment. Reports range from 0.7% to 10.3%."

A key factor in the efficacy of therapy and compliance of patients with therapy is the comfort and fit of masks. Whilst there are a large number of masks designed for adults, there are relatively few designed to suit children.

One mask designed for children is the SULLIVAN® Nasal CPAP system, Infant Nasal Bubble Mask System with Sensor tubing, manufactured by ResMed Limited. See FIG. 1. In addition, Respironics Inc. manufactures a "Comfort Flap Small Child" product.

Other infant masks are shown in the following patents: FR 2775905; GB 2277688; US 2002/0104531; U.S. Pat. Nos. 3,827,433; 4,232,476; 4,406,283; 4,774,946; 4,896,666; 4,832,015; 5,271,391; 5,318,590; 5,462,050; 5,509,408; 5,535,741; 5,813,423; 5,660,174; 6,418,929; WO 01/32250; WO 02/05883; WO 95/09023

One adult mask is the VISTA™ mask, manufactured by ResMed Limited, and described in Australian Provisional Patent Application PS1926, filed 23 Apr. 2002; U.S. 60/377, 254 filed 03 May 2002; U.S. 60/397,195 filed 22 Jul. 2002; U.S. 60/402,509 filed 12 Aug. 2002; and U.S. Ser. No. 10/391,440, 10/390,682, 10/390,681, 10/390,720 and 10/390,826, all filed 19 Mar. 2003, the contents of which are hereby incorporated by cross-reference. An ornamental design applied to the VISTA™ mask is shown in design patent application US Des 29/166,190, the contents of which are hereby incorporated by reference.

The VISTA™ mask includes a cushion, a frame, an elbow and headgear including a yoke.

While the VISTA™ mask is particularly suitable for adults, the problem arises as to how such an adult mask can be adapted to suit children.

International Patent Application WO2001/32250 (Sullivan & Wilkie) describes a mask for supplying gas under pressure to the nasal airway of an infant human. In that application, the following is stated:

". . . until now, infant masks have been developed on the basis of scaling down the adult mask to approximate to the infant face and nose. The problems with this scaling down process are threefold.

First, the adult nose and middle third of the face is very different in shape from that of the infant. The adult nose is more elongated than, and protrudes far more from the surface of the face compared to the infant nose which is relatively flat with no bridge, with the nares (nostril passages) pointing outwards. Therefore in order to fit the adult nose the base of the mask has a triangular shape elongated in the vertical axis. In contrast, with an infant, the width at the base of the nose approximates the height from the base of the nose (nares) to the apex of the nose (nasion). The proportional shape of the nasal area of an adult is rectangular compared with a square proportional shape for an infant. In addition to this basic difference in proportional shape, the adult face has quite marked contours especially around the nose and cheek area which are absent in the infant. The adult mask must therefore have acute angles which accommodate these facial contours. Thus, when an adult mask is scaled down for an infant, not only are the proportions wrong for the infant nose and face, but the angles which are unnecessarily incorporated, inadvertently introduce a new problem. Because the infant has a relatively flat nose, and virtually no bridge, the angles promote formation of channels in the sealing margin of the mask, especially in the region of the nasal bridge.

Secondly in adult mask designs, the straps of the head harness connect with lugs on the rigid manifold in the order of 20 mm away from the surface of the face to allow the mask to accommodate the height of the adult nose. Because of this a potential fulcrum effect is created. In the adult this fulcrum effect is not as problematic as in the infant, not only because the adult is less mobile during sleep . . . but also because the contours of the adult face and cheeks can offset this rise. In the infant, when the mask used is merely a scaled down adult mask, the elevation of the straps lugs above the face is about 12 mm. This by itself creates a potential fulcrum as it does on the adult but the effect is enhanced by the fact that there is no offset from the infant cheek due to the smaller facial area. Consequently, the straps holding the mask in place come into contact with the side of the face in the infant, compared to the cheek in the adult.

Thirdly, because the attachment of the paediatric mask to the face and head mimics that of the adult mask, the torsional forces are increased. The greater torsional effect is due to the decreased surface area of the mask face contact relative to the air delivery pipe. Thus relatively minor movements can result in sufficient torsional forces to cause movement at the interface between the mask and the infants face."

SUMMARY

In accordance with a first aspect of the invention a mask assembly suitable for pre-adults is provided.

In accordance with a second aspect of the invention a system of cushions, frames, headgear, yokes and other mask components are provided which fit a wide range of pre-adults with a good seal and which are economic to bring to market.

In accordance with another aspect of the invention, a system of mask cushions is provided for pre-adults in which the cushion for children aged generally 2-6 years has a shallower nasal bridge region than the cushion for pre-adults aged generally 6-16 years.

In accordance with another aspect of the invention, a system of mask cushions is provided for pre-adults in which the cushion for children aged generally 2-6 years has larger radius lower corner edges of the membrane than the cushion for pre-adults aged generally 6-16 years.

In accordance with another aspect of the invention, a system of mask cushions is provided for pre-adults aged generally 6-16 years which are adapted to be mounted to corresponding adult sized frames.

In one preferred embodiment, headgear for use with a respiratory mask includes first and second straps each adapted to be provided to a mask frame of the mask, where each of the first and second straps includes a yoke, each said yoke being constructed and arranged to accommodate at least one of a pre-adult patient or a small sized adult patient.

In another embodiment, which can be used with the headgear described above, a cushion for use with a nasal mask includes an outer membrane including a face-contact portion to form a seal with the patient; and an underlying rim positioned below the membrane, wherein the membrane and the rim are formed and positioned with respect to one another to accommodate at least one of a pre-adult patient or a small sized adult patient.

These and other aspects will be described in or apparent from the following description.

BRIEF DESCRIPTION OF FIGURES

Preferred embodiments will be described in relation to the following drawings, in which:

FIGS. 38a-38f are various cross-sections thereof;

DETAILED DESCRIPTION OF PREFERRED EMBODIMENTS

Figure 1:
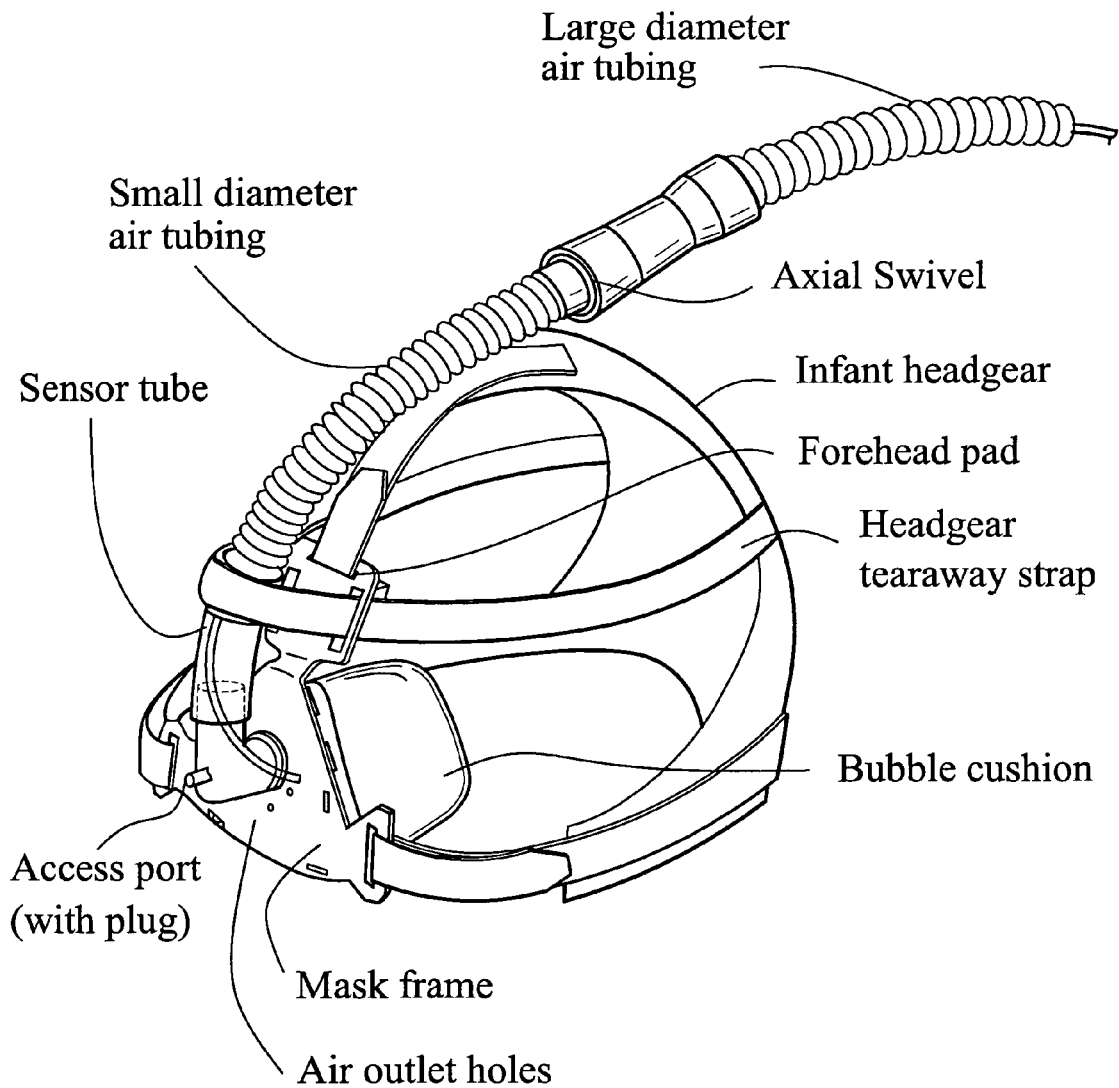
FIG. 1 shows related art infant bubble mask.
Figure 2:
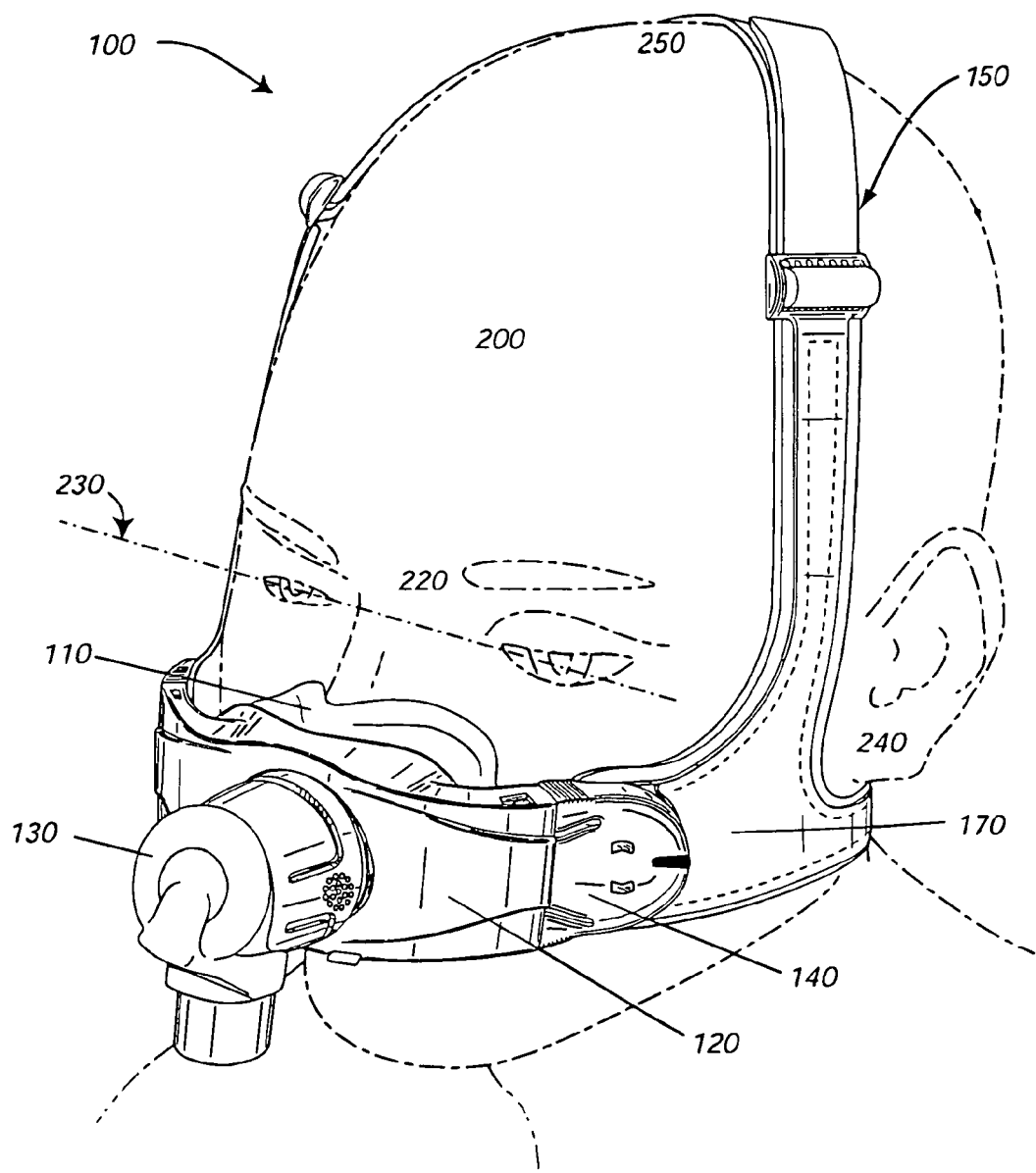
FIG. 2 shows a perspective view of a related art VISTA™ mask on an adult patient.
Figure 3:
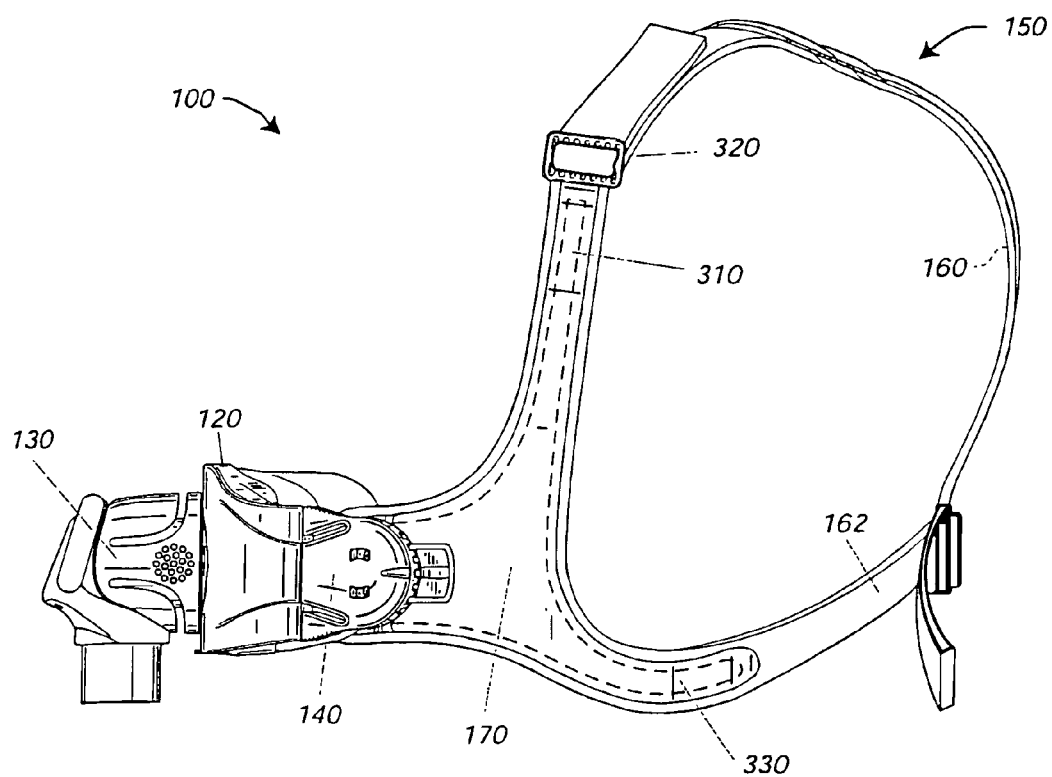
FIG. 3 shows a side view of the VISTA™ mask.

FIGS. 2-5 illustrate a related art mask known as the VISTA™, manufactured by ResMed Incorporated. Mask assembly 100 comprises (i) a soft face-contacting cushion 110, (ii) swivel elbow 130, (iii) headgear clips 140, (iv) a frame 120 adapted to receive the cushion 110 and support swivel elbow 130 and headgear clips 140, and (v) headgear 150 including straps 160 and a headgear yoke 170.

Stabilization of the cushion 110 and frame 120 on the face 220 of an adult patient 200 is assisted by the size, shape and positioning of the yoke 170 on the headgear 150. In spite of the problems identified by Sullivan & Wilkie concerning the fulcrum and torsional effects of prior art masks, greater stability can be achieved in pre-adults with a mask in accordance with the present invention. In one embodiment, the present inventors have redesigned the VISTA™ mask in FIGS. 2-5 to be suitable for use with pre-adults, or adults with small or child-like facial features.

FIGS. 6-16 illustrate components of a mask system for use with pre-adults, in accordance with preferred embodiments of the present invention, in which like elements are referenced by like elements compared to the VISTA™ shown in FIGS. 2-5.

The US Food & Drug Administration (FDA) makes the following classifications for pre-adults:

TABLE 1

| | |
|---|---|
| Neo-natal | 0-1 month |
| Infant | 1 month-2 years |
| Child | 2 years to 12 years |
| Adolescent | 12 years to 16 years |

In accordance with an aspect of the invention, a mask system is provided which uses a different classification:

TABLE 2

| | |
|---|---|
| Infants | 0-2 |
| Mini | 2-6 |
| Kid | 6-16 |

The mask system can fit the same range of pre-adults defined by the FDA, however, four separate mask systems are not required.

In adults, a system of masks suitable for fitting a range of people should take into account body mass and racial nose characteristics. For example, the East Asian-shaped nose typically has a lower nasal bridge region compared to the Caucasian-shaped nose. However, below the ages of 5-7 there are few racial distinctions in children. In particular, neo-nates, infants and young children have no nasal bridge. Not only do children have smaller heads and faces than adults, their heads and faces are differently shaped. In accordance with an aspect of the invention, a system of mask & headgear sizes has been developed in which a minimal set of components can be used to fit the widest range of people:

TABLE 3

| | Cushion 110 | Frame 120 | Yoke 170 | Clips 140 | Elbow 130 |
|---|---|---|---|---|---|
| Mini (2-6YO) | 2-3 sizes | 50-70% of standard | Extra-small | 50-70% of standard | 50-70% of standard |
| Kid (6-16YO) | 2-3 sizes | Standard | Small | Standard | Standard |

An advantage with the mask system described herein is that a very wide range of pre-adults can find a mask which fits well with little leak, is comfortable, and yet is economic for manufacturers to produce and bring to market. Since the pediatric, small adult, or pre-adult market is relatively small in comparison to the standard adult market, there is a reduced economic incentive for business to bring product to the market. However, when a system in accordance with the invention is produced, it becomes more economically viable to produce such masks.

Headgear Yoke Design

Figure 6:
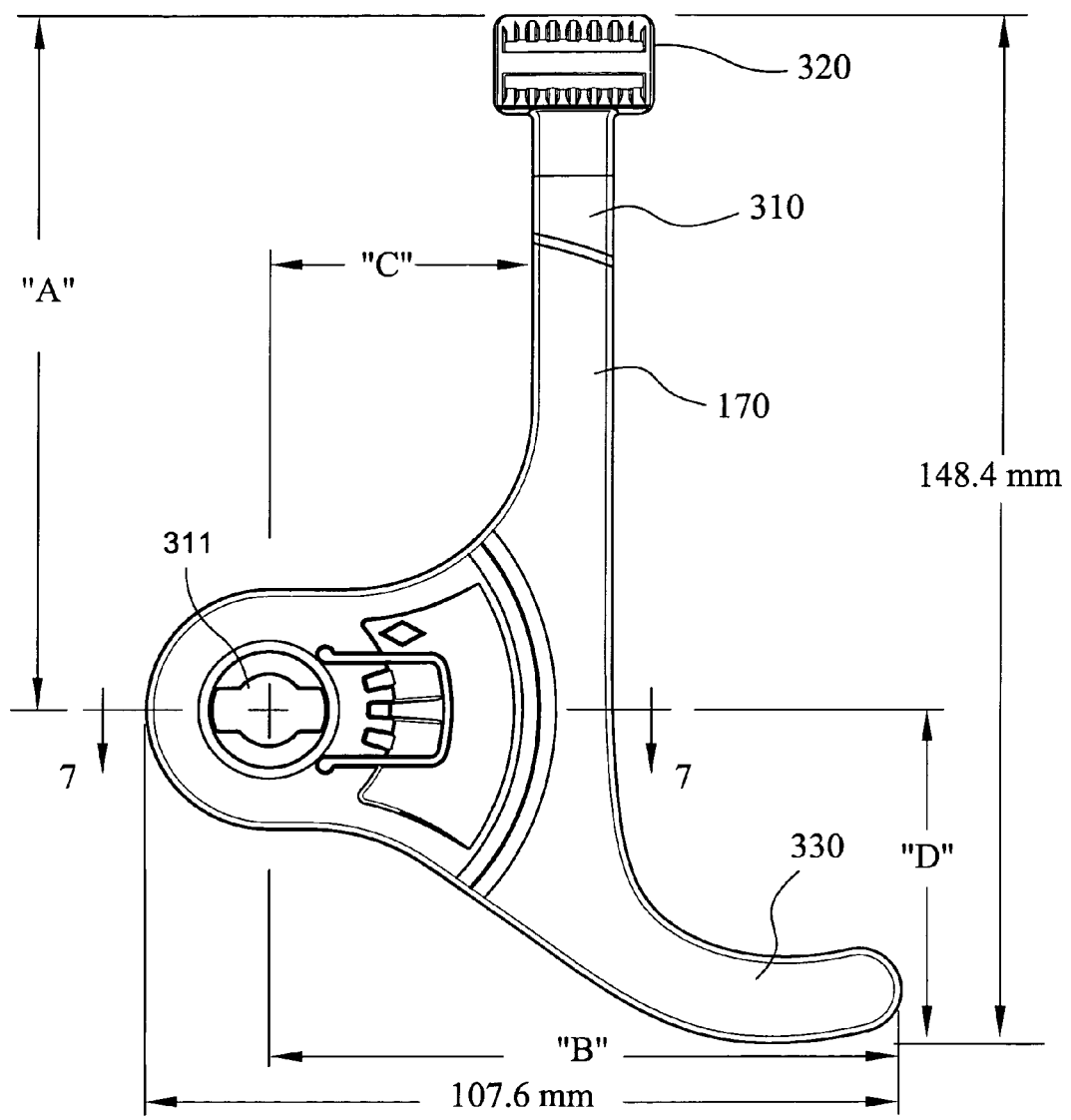
FIG. 6 shows a plan view of a headgear yoke in accordance with a first embodiment of the invention.
Figure 7:
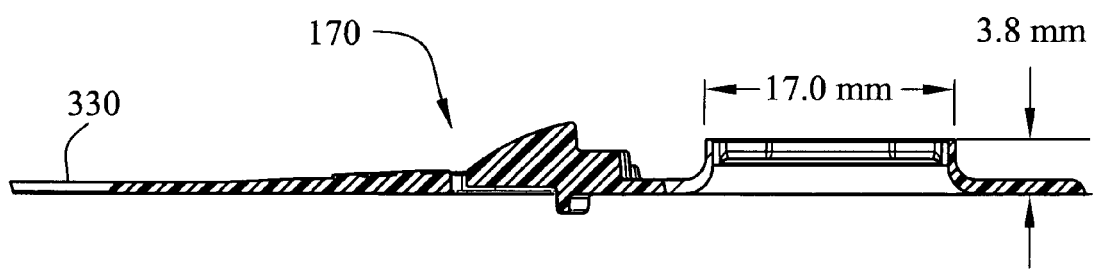
FIG. 7 is a cross-sectional view taken along section 7-7 in FIG. 6.
Figure 8:
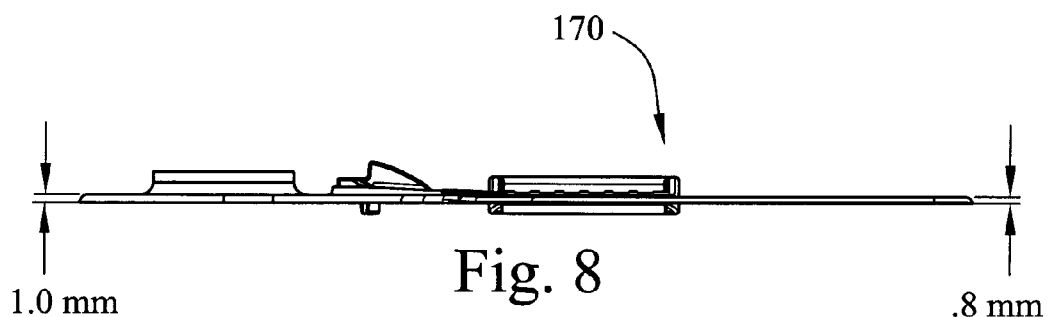
FIG. 8 is a bottom view of the yoke shown in FIG. 6.

FIGS. 6-8 illustrate (left hand) headgear yoke 170 suitable for pre-adults in accordance with an embodiment of the invention. Yoke 170 includes vertical finger 310, ladder lock 320 to receive a headgear strap, lower yoke finger 330 and key-shaped recess 311 to receive a clip 140 (see FIG. 3). Headgear yoke 170 preferably should have one or more of the following features:

1. yoke vertical finger 310 located midway between eye-line 230 and earlobe 240 (refer to FIG. 2).
2. yoke ladderlock 320 located ⅓ of the distance between the eye-line 230 and crown of the head 250.
3. a gap of 5 mm maintained between lower yoke finger 330 and lowest point of earlobe 240.
4. lower yoke finger 330 positioned about 15 mm behind the lowest point of the earlobe 240.
5. a lower yoke finger 330 positioned at an angle of about 15-20°, preferably 17°, like the VISTA™.

Table 4 compares dimensions of related art VISTA™ headgear yoke with two "small" headgear yokes, referred to as the "Mini" and "Kid," in accordance with preferred embodiments of the invention. The first row of Table 4 identifies four features (A, B, C and D) of the headgear yoke. These features are shown in FIG. 6, while FIGS. 7 and 8 show additional views of the yoke 170. The dimension values can be varied up to ±20%, and preferably up to ±10%, of the dimensional values listed in Table 4 below and shown in the Figures. For example, distance A can be about 90-100 mm, distance B can be about 80-100 mm, distance C can be about 25-40 mm, and distance D can be about 45-55 mm, although other distances are possible.

Figure 4:
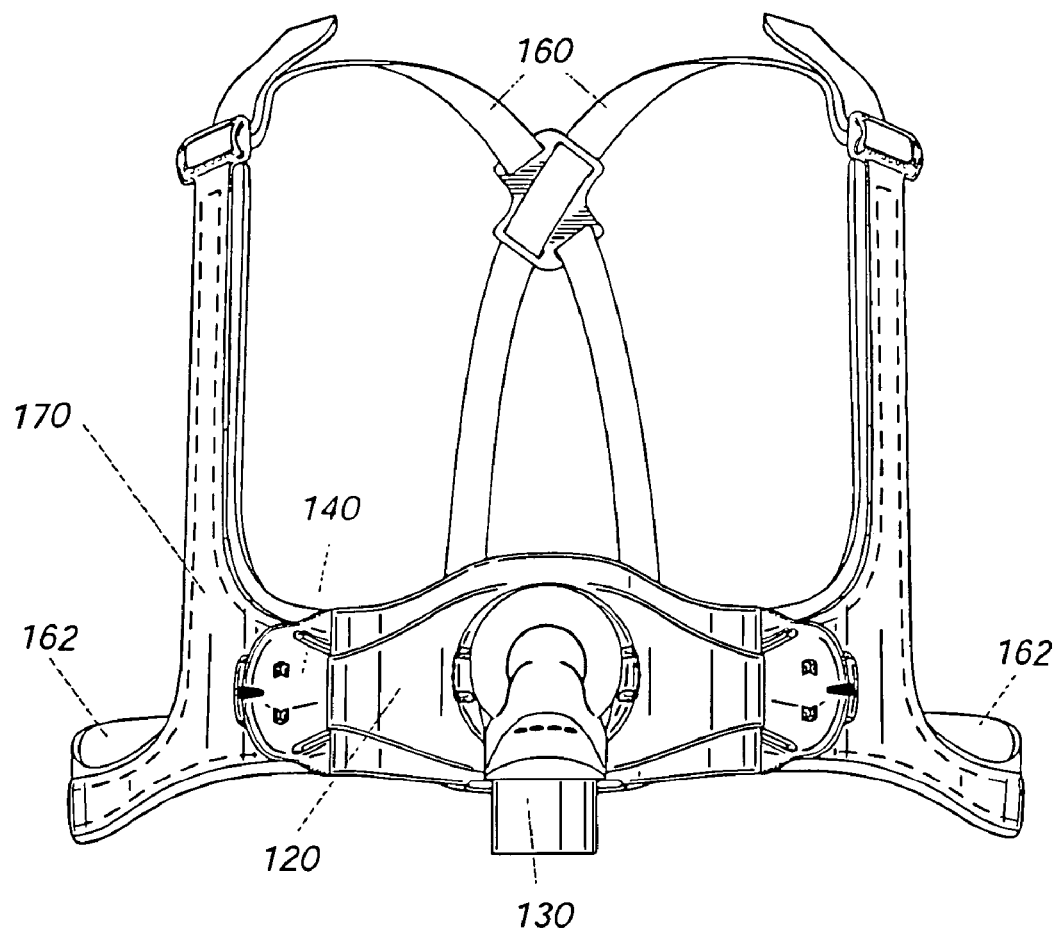
FIG. 4 shows a front view of the VISTA™ mask.
Figure 10:
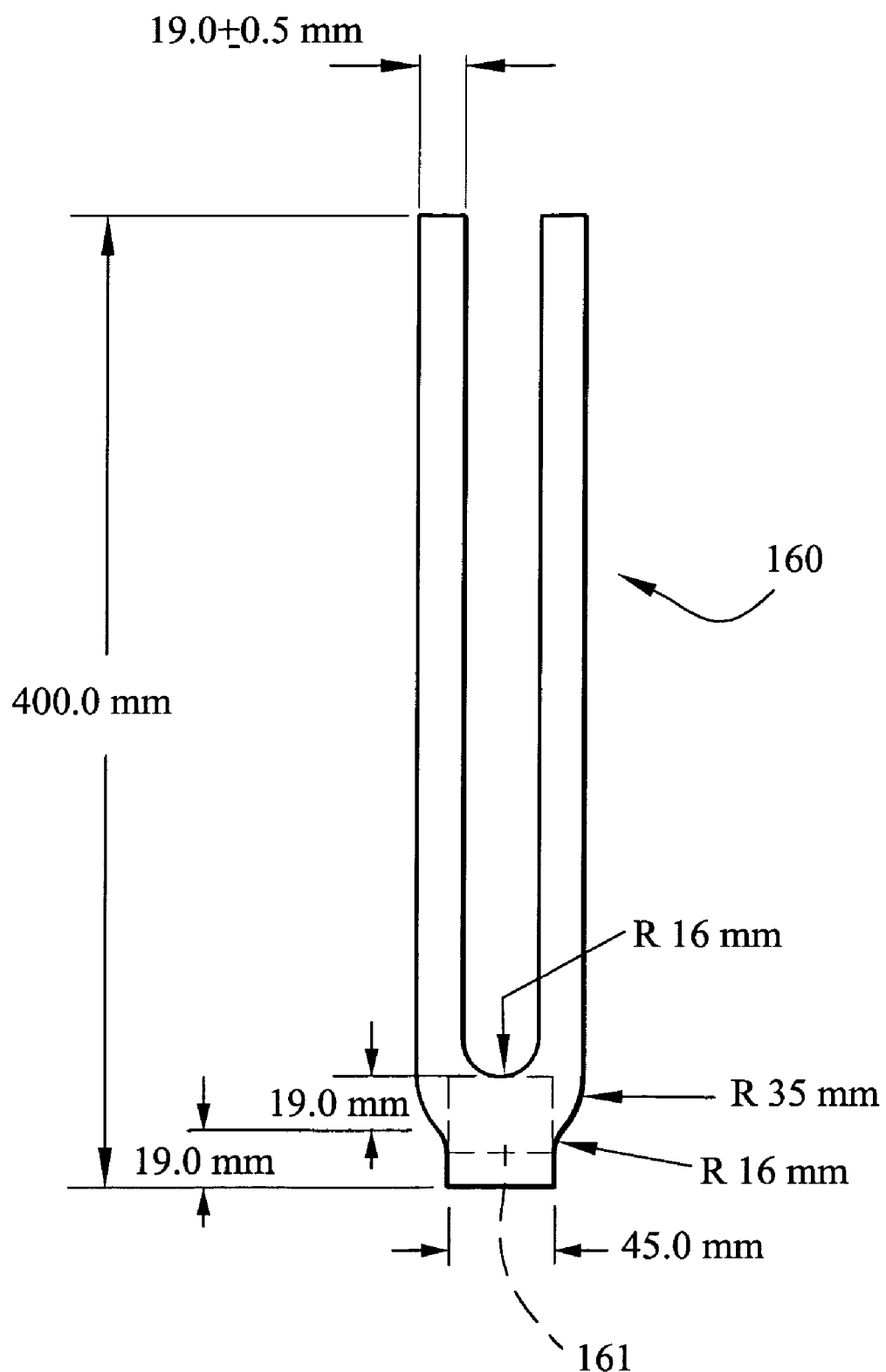
FIG. 10 is a plan view of a central rear headgear strap according to an embodiment of the present invention.
Figure 11:
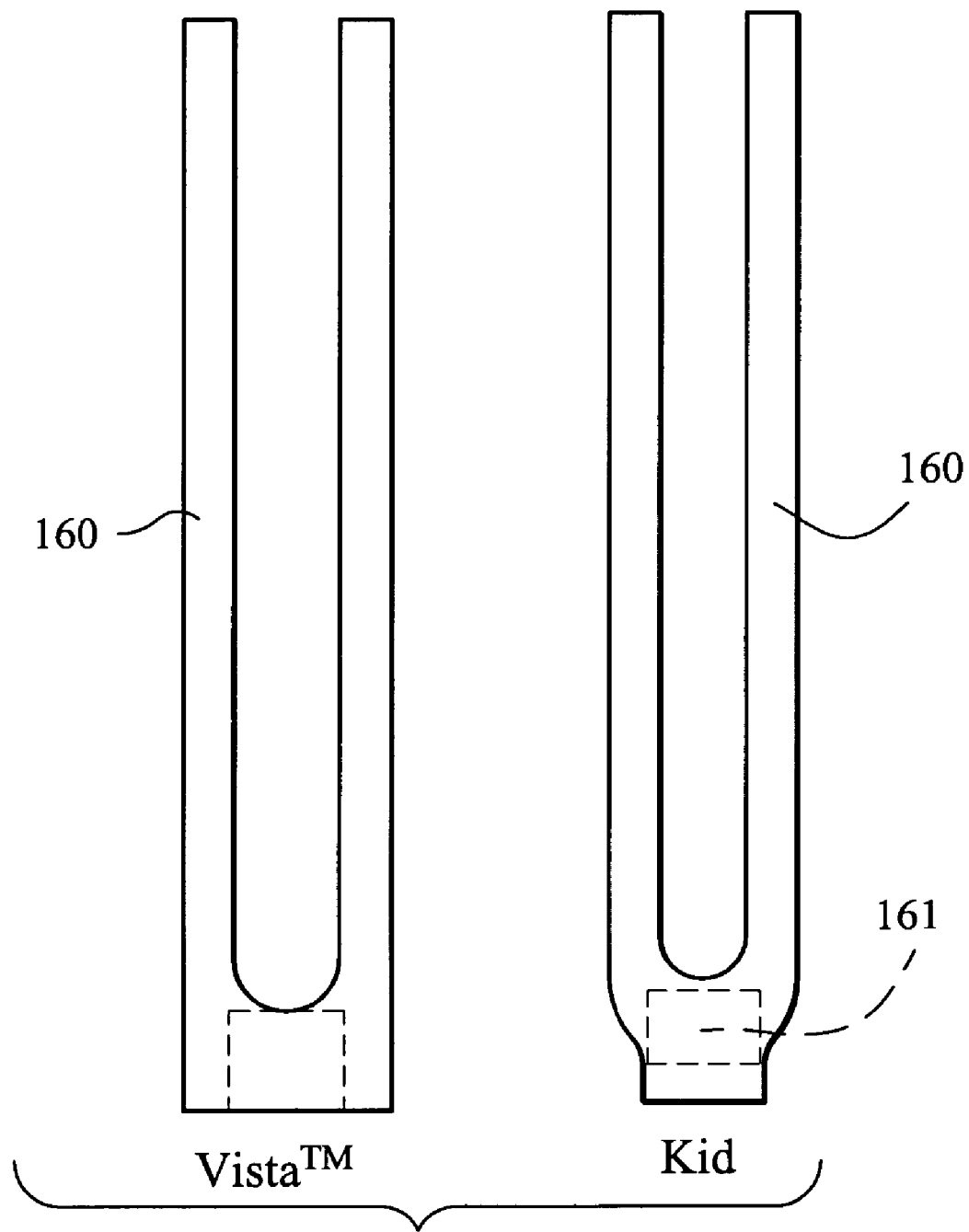
FIG. 11 is a plan view comparing the central rear headgear strap of FIG. 10 and the VISTA™.
Figure 11A:
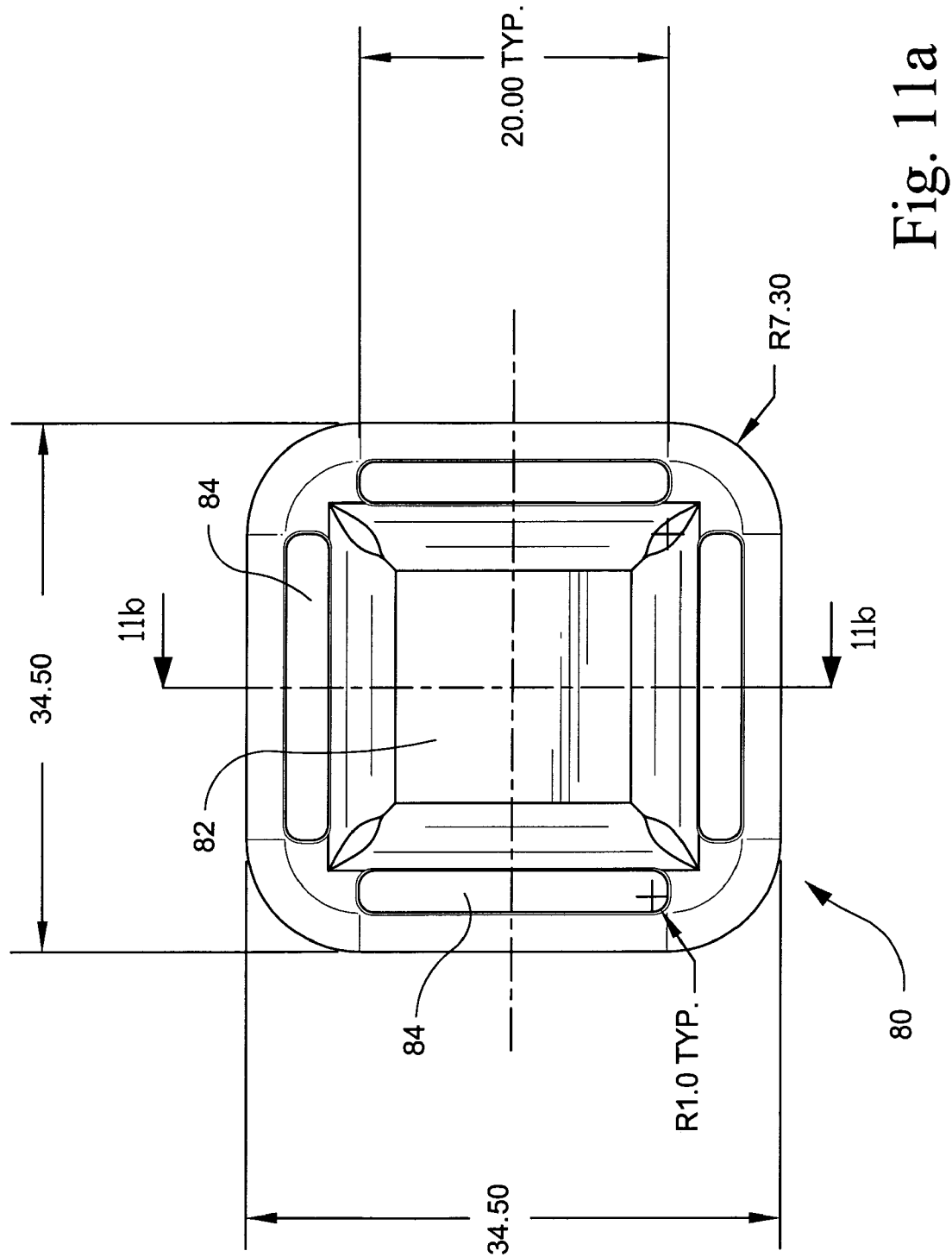
FIGS. 11a-11c illustrate a headgear crossover according to an embodiment of the present invention.
Figure 11B:
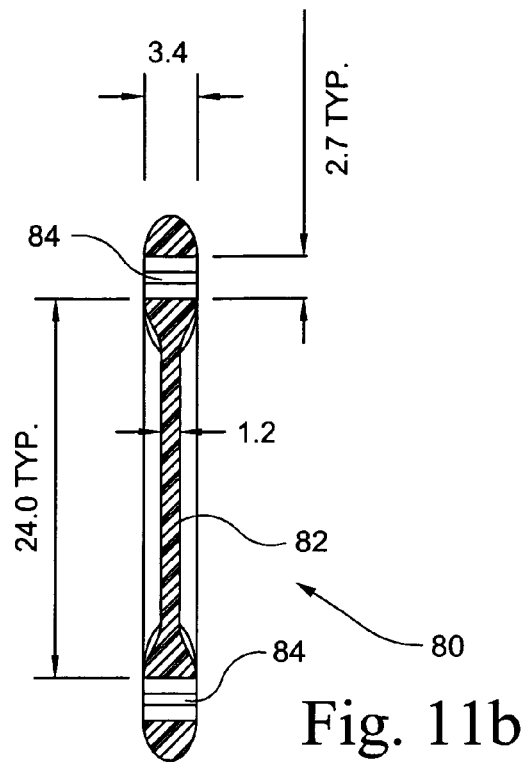
Figure 11C:
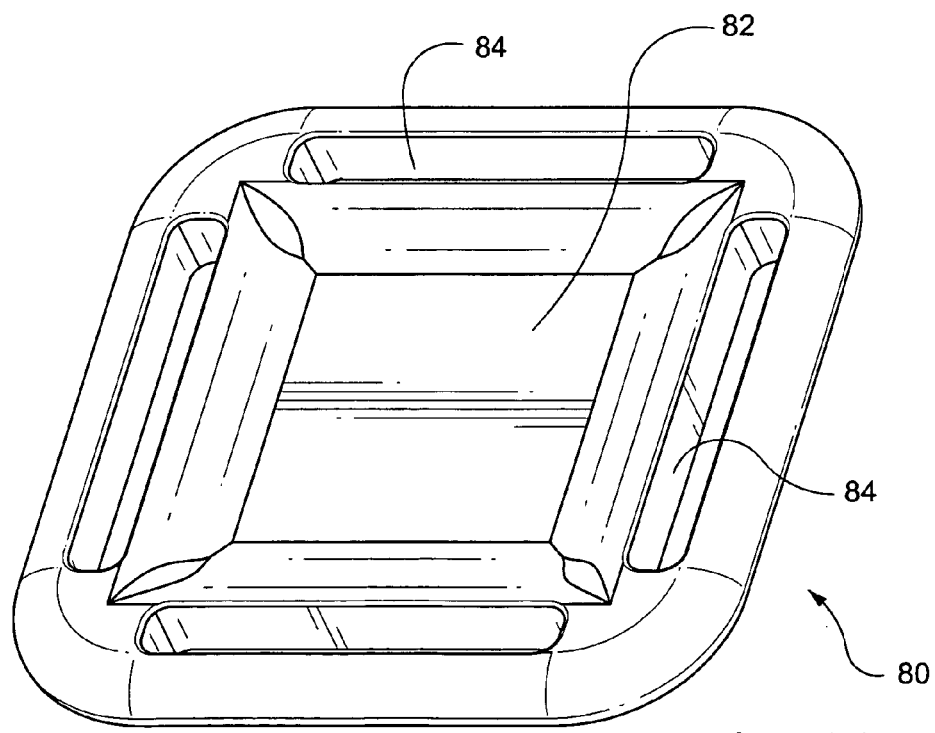

FIGS. 11a-11c illustrate a headgear crossover 80 that can be used instead of the crossover shown in FIG. 4. The crossover 80 includes a main body 82 which may have a substantially square appearance, although other shapes are possible. Each side may include a slot 84 to receive one of the straps 160 shown in FIGS. 10 and 11. Exemplary dimensions are shown in FIGS. 11a-11c, although other dimensions are possible. Crossover 80 has an improved appearance compared to crossover in FIG. 4. Further, crossover 80 provides greater friction to the straps running through it and so resists slipping out of place more than the crossover in FIG. 4. For example, the sliding force for the crossover 80 may be increased between about 100-150%.

TABLE 4

Yoke Comparison

|  | "A" (mm) | "B" (mm) | "C" (mm) | "D" (mm) |
|---|---|---|---|---|
| VISTA ™ (related art) | 130 | 110 | 43 | 48.5 |
| "Small" 1st embodiment - "Mini" | 100 | 86 | 28 | 46 |
| "Small" 2$^{nd}$ embodiment - "Kid" | 100 | 95 | 37 | 49 |
| "Small 3$^{rd}$ embodiment - "Kidsta-S" | 100 | 90 | 37 | 49 |

Headgear Strap Design

Figure 5:
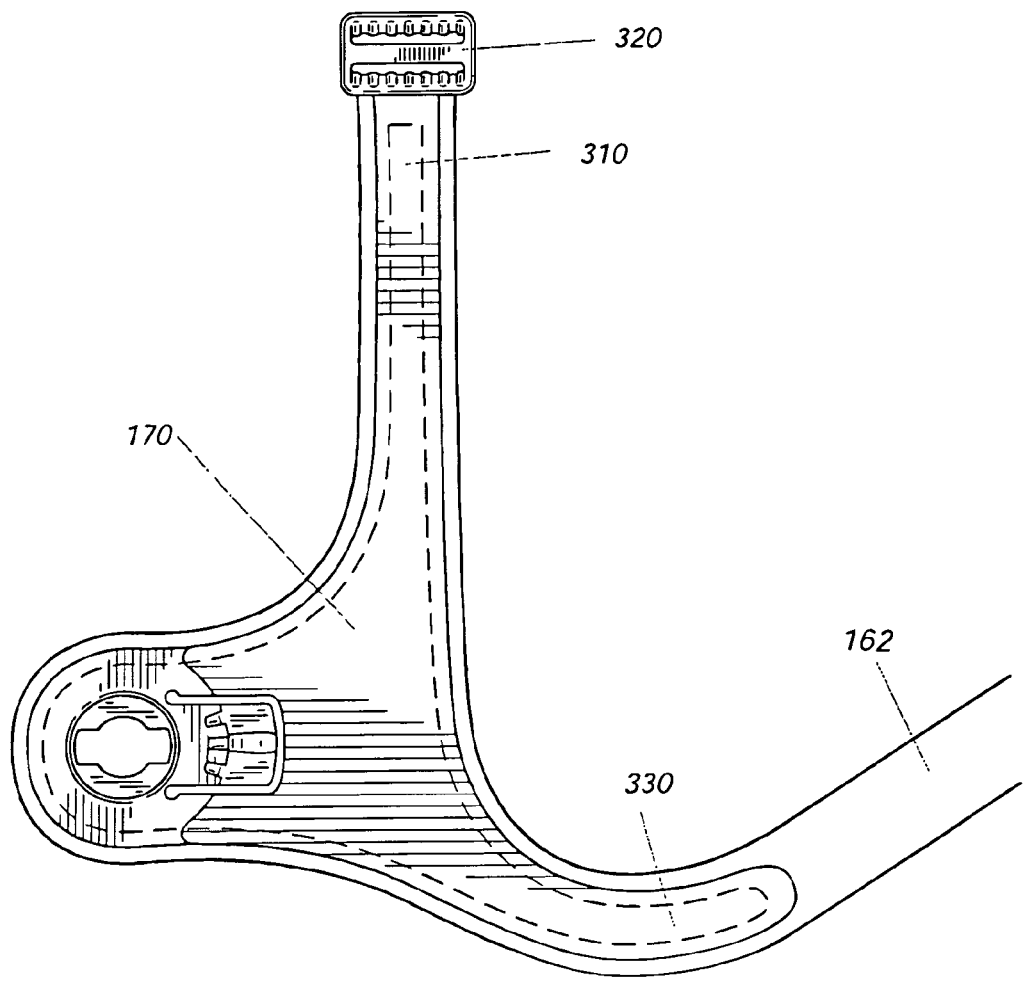
FIG. 5 shows a side view of a headgear yoke of the VISTA™ mask.
Figure 9:
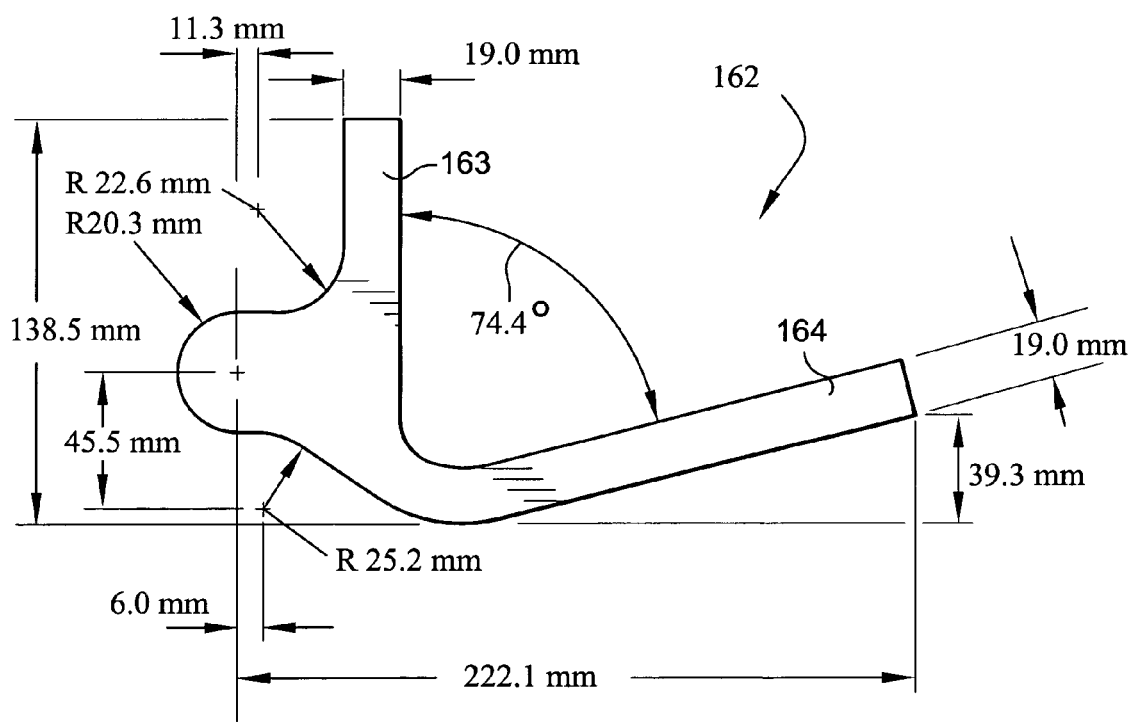
FIG. 9 is a plan view of a side headgear strap according to an embodiment of the present invention.

FIG. 9 illustrates a side headgear strap 162 suitable for use with yoke 170 shown in FIG. 6. Strap 162 includes vertical portion 163 and lower portion 164. The yoke is mounted on strap 162 in a manner similar to that shown in relation to the VISTA™ yoke and strap, as shown in FIG. 5. For example, the yoke and strap can be secured to one another via stitching, adhesives, etc.

The headgear strap 162 may include the dimensions as shown in FIG. 9. However, those dimension are exemplary only, as other dimensions could be used instead. For example, the strap 162 could have dimensions that are varied up to ±20%, but preferably no more than up to ±10%, of the dimensional values shown in the example in FIG. 9. Other variations to the yoke are described below, which may also impact the dimensions of the headgear strap.

FIG. 10 shows a center strap 160 for the headgear 150. Preferred dimensions of the center strap 160 are illustrative only, and may be adjusted up to +/−10%-20% of the values shown. FIG. 11 shows the center strap 160 of the "Kid" in side-by-side comparison with the VISTA™ center strap. The rear width of the center strap 150 shown in FIG. 10 can be reduced by about 30 mm, as compared to the VISTA™ center strap. Further, the center strap 150 can accommodate a label (in label area 161) and ladder locks.

Cushion Design

Figure 12:
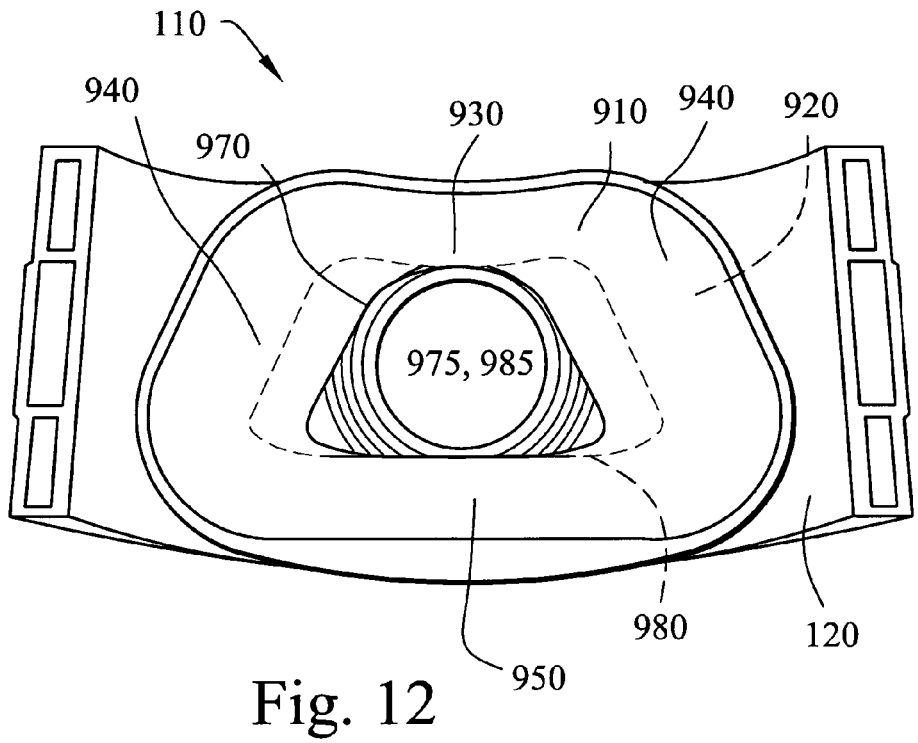
FIG. 12 shows a plan view of a cushion, mounted on a frame, in accordance with an embodiment (the "Kid cushion") of the invention.
Figure 13:
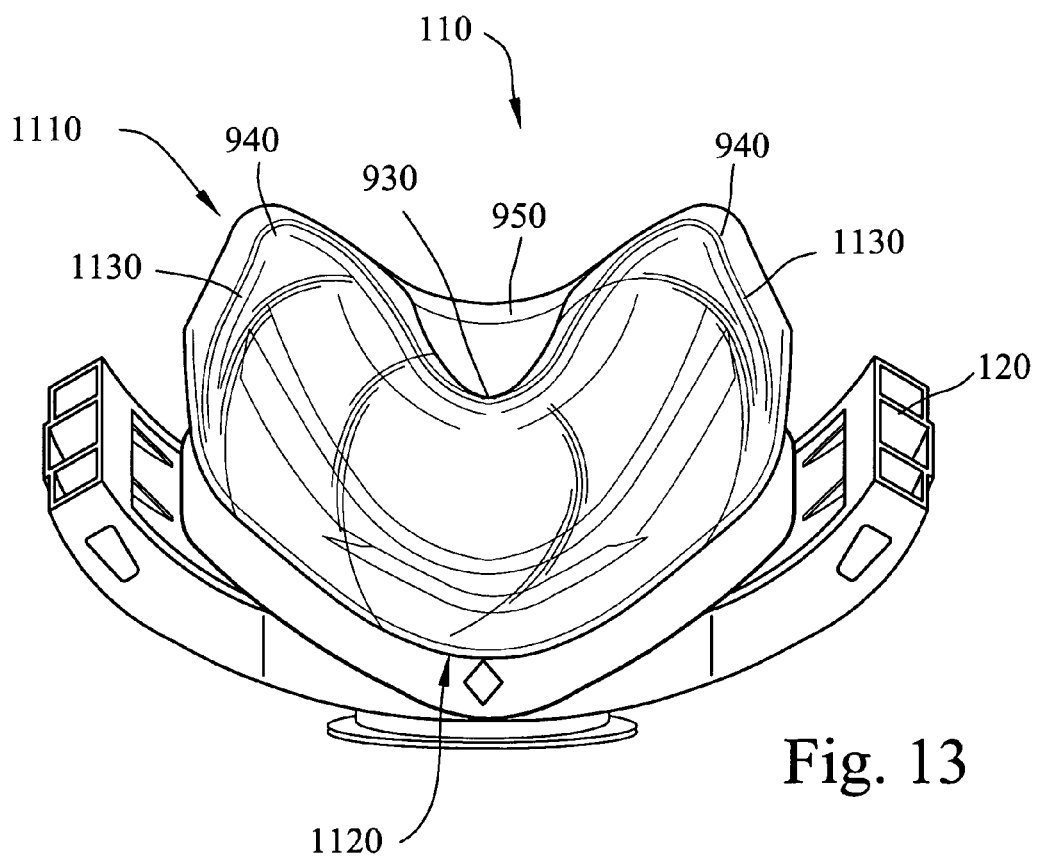
FIG. 13 shows a top elevation view of the "Kid" cushion.
Figure 14:
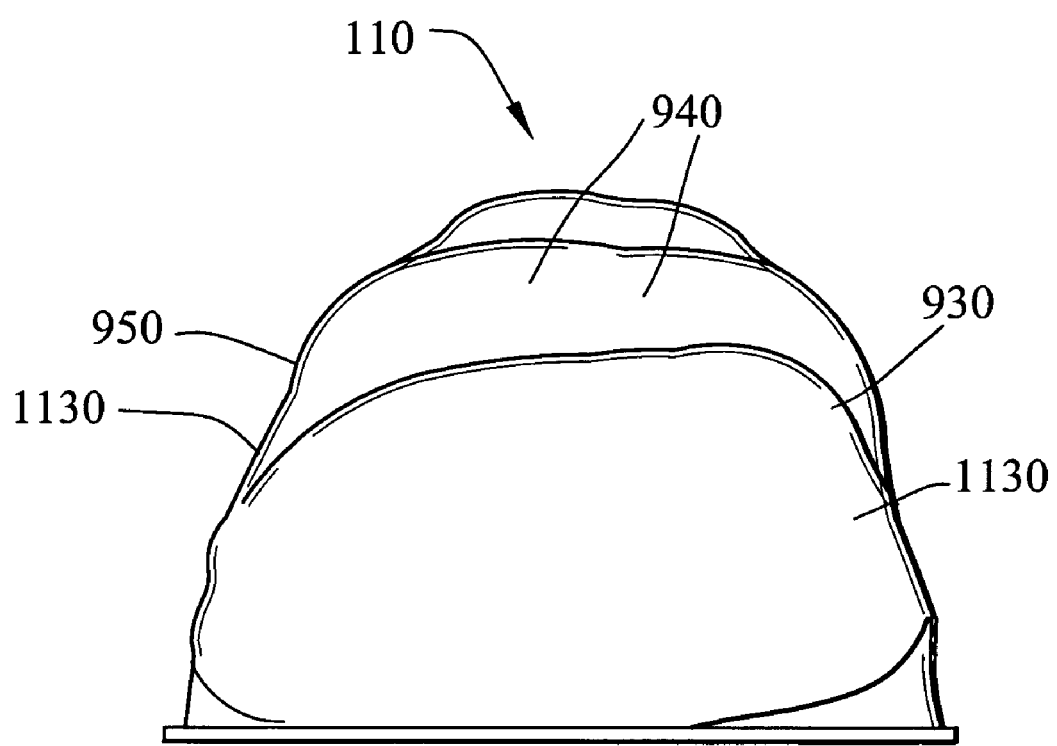
FIG. 14 shows a side elevation view of the "Kid" cushion (without the frame)
Figure 15:
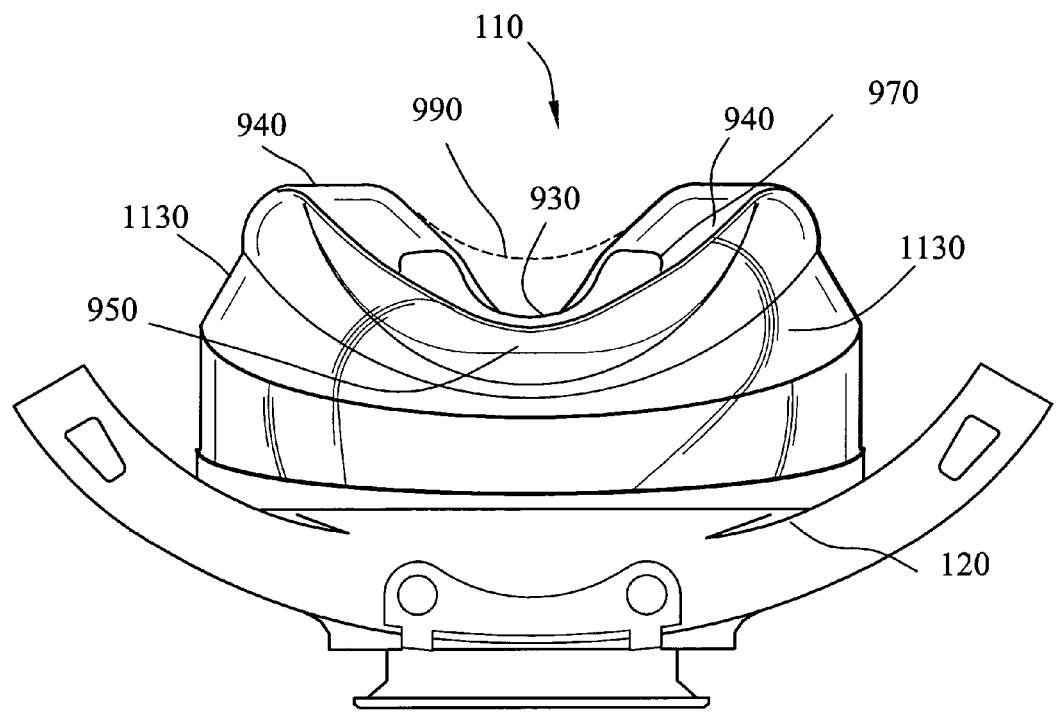
FIG. 15 shows a bottom elevation view of the "Kid" cushion.
Figure 16:
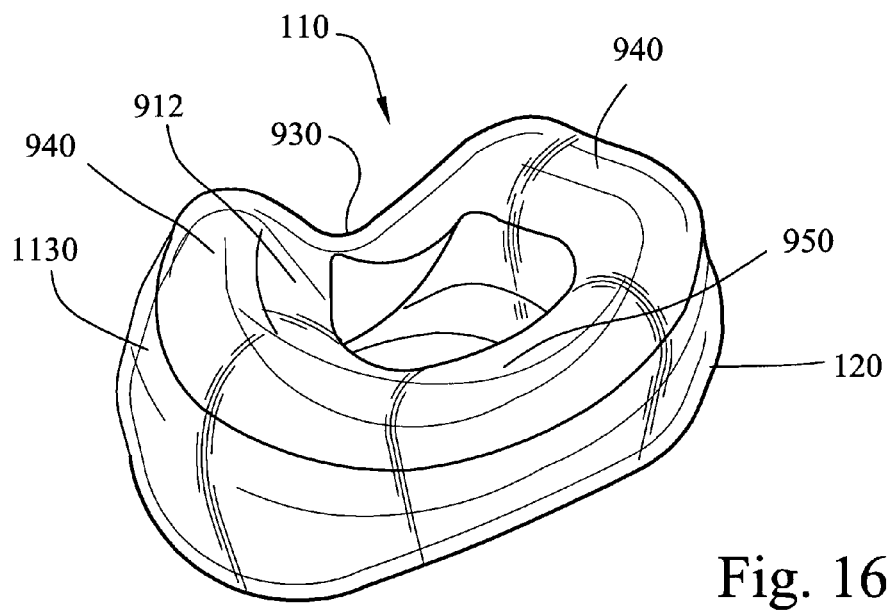
FIG. 16 shows a perspective view of the "Kid" cushion.

FIGS. 12-16 illustrate a cushion 110 in accordance with an embodiment (e.g., the "Kid") of the present invention. FIGS. 12-13 and 15 show the cushion mounted on a standard VISTA™ frame 120. Cushion 110 includes a double-walled face contacting portion. As shown in FIG. 12, the double wall includes a thin flexible outer membrane 910 which forms a sealing structure, and an underlying rim 920 which forms a support structure. In FIG. 12, the rim 920 is indicated with a broken line as it is seen through and/or below the membrane 910. As shown in FIG. 13, a top view, cushion 110 has a patient contacting region 1110 and a frame-engaging region 1120. The cushion 110 and frame 120 are adapted to engage with one another as in the VISTA™ mask, as described in U.S. Patent Application No. 60/402,509, or other ones of the applications listed above, although other engagement methods are possible. Both the membrane 910 and rim 920 preferably include a nasal bridge notch 930, a pair of side portions 940, and a curved lip region 950, as shown in FIG. 12.

The cushion 110 is constructed from a silicone material, such as that used for the VISTA™ mask, although other materials could be used, e.g., gel, foam, silicone and combinations thereof.

In accordance with an embodiment of the invention, 2-3 "Kid" cushion sizes and 2-3 "Mini" cushion sizes can be used to fit pre-adults from 2 to 16 years.

Since the "Kid" range of cushions fit adult VISTA™ frames, e.g., see frame 120 in FIGS. 2-5, 12, 13 and 15, they have a generally inwardly sloping outer wall 1130 (see FIGS. 13-16) that provides a transition between the relatively smaller patient-contacting region 1110 and the frame-engaging portion 1120 of the cushion 110. The outer wall can also be stepped as well. In either case, the area of the bottom of the cushion (where it connects to the frame) is projected wider than the area where the membrane contacts the facial tissue. The difference in area (i.e., the projected area of the bottom of the cushion) can help reduce the pressure needed to maintain a seal with the face. This is an advantage especially in regard to fitting pre-adult or small adult patients, where the available patient contact area may be limited.

Moreover, the smaller area covered by the Kidsta Small and Kidsta Extra Small masks results in reduced headgear loading. The smaller area of face exposed to the air pressure in the mask results in a smaller overall reaction force, as force is equal to pressure by area. The reaction force from the pressure in the mask is a significant component of the load on the mask, especially at higher air pressures. Hence the total load on the mask, and the headgear strap loads required to match this load, will be less with the small mask area.

Both the "Kid" and "Mini" range of cushions are not only smaller than adult range of VISTAT™ cushions, they have a different shape. For example, both the "Kid" and "Mini" cushions have relatively shallower notches in the nasal bridge region and relatively shallower curves in the lip region compared to an adult VISTA™ cushion. See also FIGS. 27, 28, 31, 32 and 34.

Table 5 shows the change in size of a "Kid" cushion in accordance with one embodiment of the invention. The membrane 910 of the cushion 110 has an orifice 975 (FIGS. 12 and 17) defined by the edge 970 of the membrane 910. There is a corresponding orifice 985 (visible through the membrane 910) defined by the edge 980 of the rim 920. In use, the nose of the patient 200 passes through the orifice 975.

Figure 17:
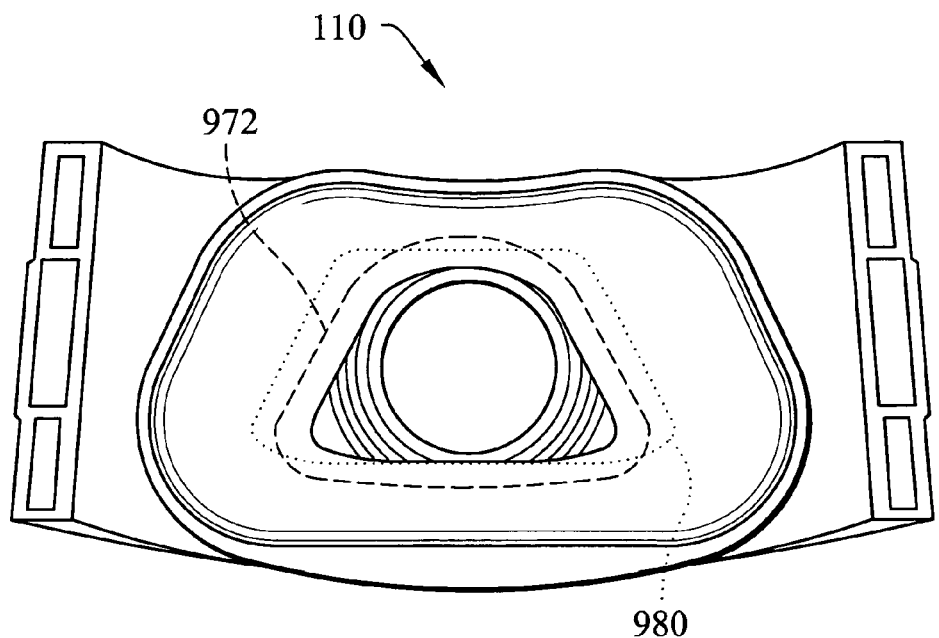
FIG. 17 shows a plan view of the "Kid" cushion compared to other cushion shapes.
Figure 18:
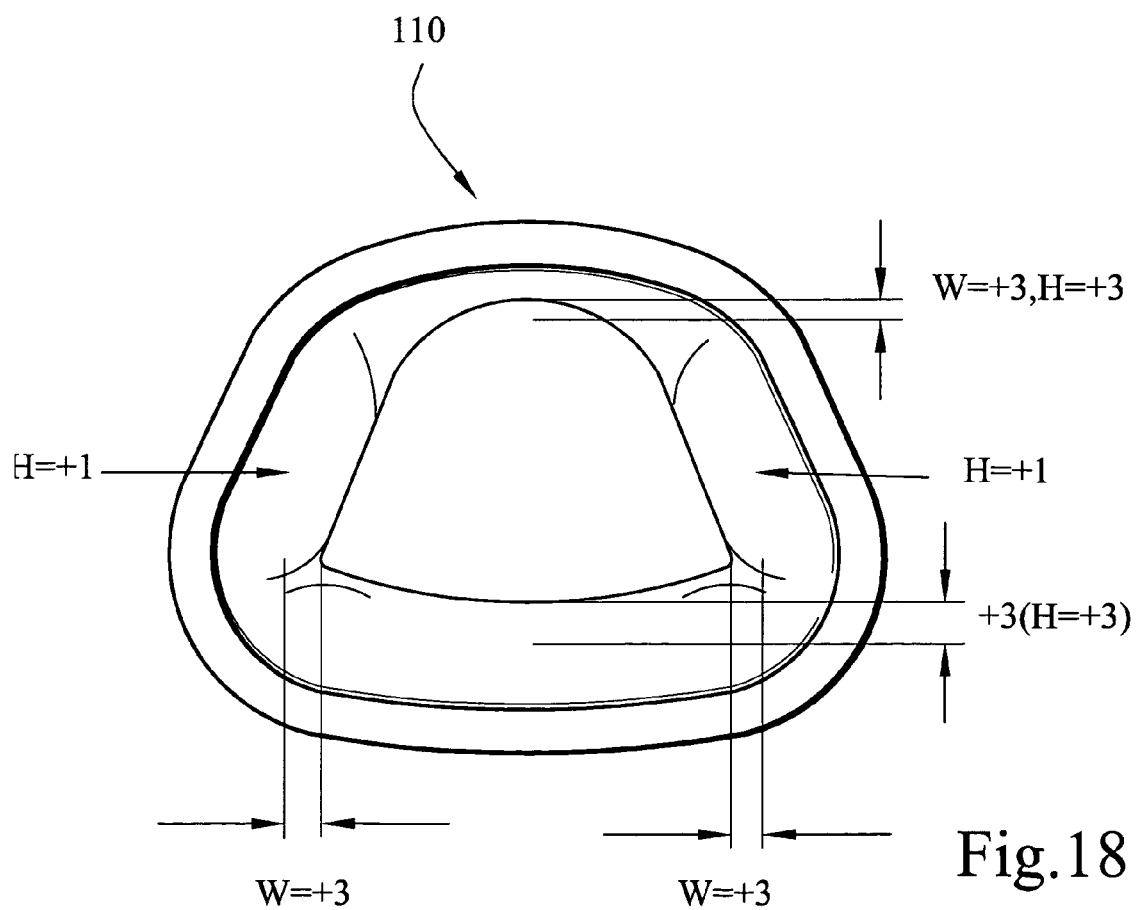
FIG. 18 shows a rear review of an underlying rim of the "Kid" cushion showing the change in dimension compared with an adult VISTA™.
Figure 19:
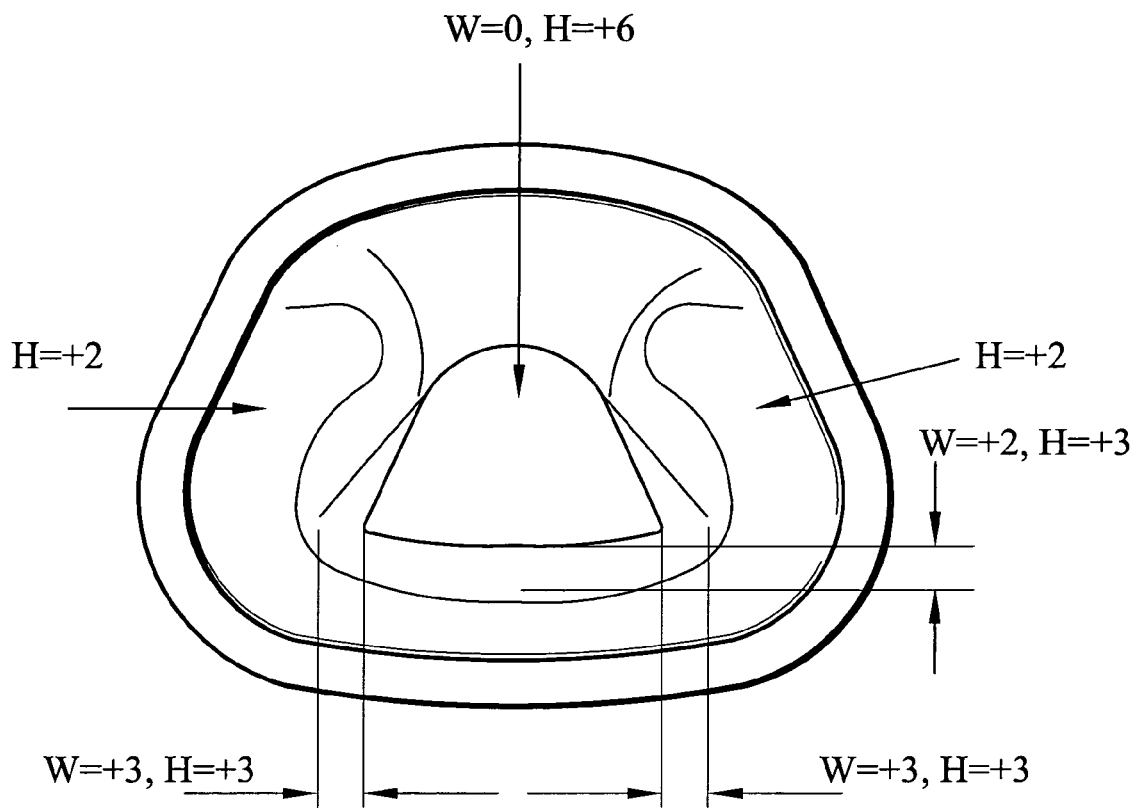
FIG. 19 shows of a membrane of the "Kid" cushion showing the change in dimension compared with an adult VISTA™ cushion.

As compared to the VISTA™ cushion, the orifice 985 of the rim 920 is about 3 mm smaller all around its perimeter, however the membrane 910 is smaller by an amount varying from about 0 to 3 mm. FIG. 17 shows broken line 972 which indicates the general position of the edge of the membrane in a corresponding adult size VISTA™ cushion with its corresponding larger orifice. FIG. 18 schematically shows relative changes of the rim of the "Kid" cushion compared to the VISTA™ cushion, while FIG. 19 schematically shows relative change in the membrane of the "Kid" compared to the VISTA™. The relative changes in height of the cushion reflect the relatively shallower notch in the nasal bridge region and the relatively shallower curve in the lip region.

TABLE 5

"Kid" v. VISTA ™+0—Cushion Comparison

|  | Membrane | Rim |
|---|---|---|
| Orifice span | 0 mm in nasal bridge region<br>−2 mm in lip region<br>−3 mm in side region | −3 mm in all regions |

TABLE 5-continued

"Kid" v. VISTA ™+0—Cushion Comparison

| | Membrane | Rim |
|---|---|---|
| Height of patient contacting region from frame-engaging portion. | +6 mm in nasal bridge region<br>+3 mm in lip region<br>+2 mm in side region | +3 mm in nasal bridge region<br>+3 mm in lip region<br>+1 mm in side region |
| Kid Orifice span | nasal bridge region—23<br>lip region—31<br>side region—19 | nasal bridge region—35<br>lip region—33<br>side region—43 |
| Kid Height of patient contacting region from frame-engaging portion | nasal bridge region—28<br>lip region—20.7<br>side region—34 | nasal bridge region—14<br>lip region—16<br>side region—26 |

In accordance with another embodiment of the invention, a "Kid" cushion has a further 3-4 mm increase in height of the membrane in the patient contacting-portion from the frame-engaging portion in the nasal bridge region, hence a total of 9-10 mm when compared to an adult cushion. There is a corresponding change in the rim.

Figure 20:
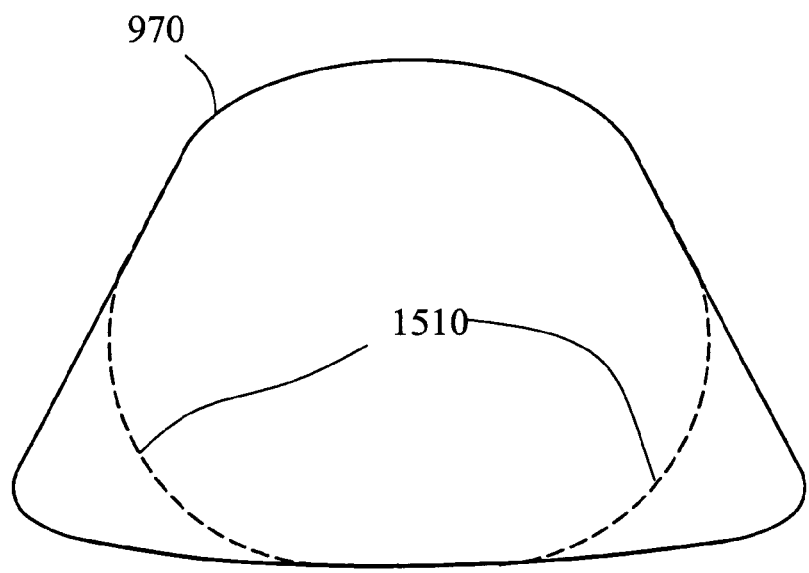
FIG. 20 shows the edge of the membrane of the "Kid" cushion and the more rounded lower corners of the "Mini" cushion.

In accordance with another embodiment of the invention, a "Mini" cushion has a further 6-7 mm increase in height of the membrane in the patient contacting-portion from the frame-engaging portion in the nasal bridge region, hence a total of 12-13 mm when compared to an adult cushion. There is a corresponding change in the rim. In this way, a "Mini" cushion has an even shallower notch in the nasal bridge region compared to a "Kid" cushion. Since a "Mini" cushion uses a smaller frame than a "Kid" cushion, it does not have the generally sloping outer wall in the transition region between the face-contacting portion and the frame-engaging portion. Furthermore, the "Mini" cushion is generally closer to the face for better stability. Such a shallower notch is indicated by broken line 990 in FIG. 15. Furthermore, as shown in FIG. 20 the lower corners of the "Mini" cushion 1510 are more rounded (i.e. larger radius) than the corresponding corners of the "Kid" cushion. The cushion includes a nasal ridge region, a top lip region and two side regions. In this example, the membrane and rim each have an orifice in which a width of the membrane orifice is between about 30 and 32 mm in the lip region, between about 18 and 20 mm in each side region, and between about 22 and 24 mm in the nasal bridge region, a width of the rim orifice is about 34 and 36 mm in the nasal bridge region, between about 32 and 34 mm in the lip region, and between about 42 and 44 mm in each side region of the cushion. The membrane and the rim each have a height as measured from a portion of the cushion that engages the frame. The membrane height is about 27 and 35 mm in the nasal bridge region, between about 19 and 22 mm in the lip region, and between about 33-35 mm in each said side region, the rim height is between about 13 and 18 mm in the nasal bridge region and the lip region, and the rim height in each said side portion is between about 25 and 27 mm.

In general the materials used to construct a mask assembly in accordance with the invention are the same as those used to construct the VISTA™ mask.

Figure 21:
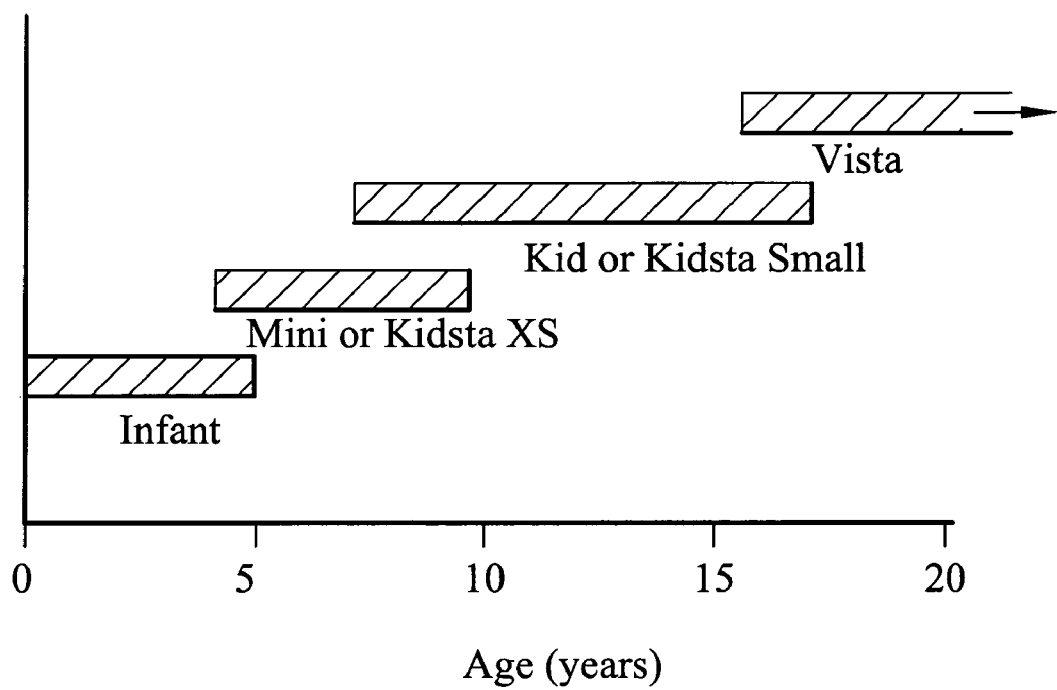
FIG. 21 shows a sketch plot of a system of masks in accordance with an embodiment of the invention.

As shown in FIG. 21, there may be some overlap in ages between the different masks and cushions. For example, some pre-adults aged 7 years may find a "Mini" (shown as "Mini-" in FIG. 21) mask too small and it may be appropriate for them to be fitted with a "Kid" (shown as "Kid" in FIG. 19). Of course, the Mini and Kid may be used for adult patients having smaller facial shapes or pre-adult features.

Further Embodiments

Further cushion embodiments of the invention are described in relation to FIGS. 22-45. These embodiments also relate to shrinking and/or re-proportioning the VISTAT™, Kid or Mini cushion to create "small" ("Kidsta Small") and "extra small" ("Kidsta Extra-Small (XS)") cushion sizes, while preferably maintaining the same basic architecture for fitting the cushion to the VISTA™ mask frame. The new embodiments have been developed as a result of conducting testing on the "Kid" and "Mini" cushions described above.

Figure 22:
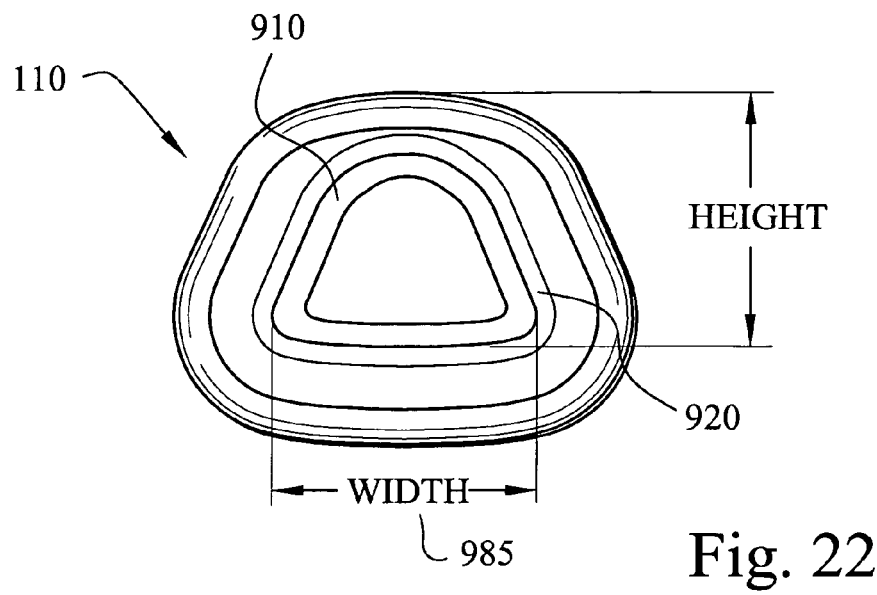
FIG. 22 illustrates a rear view of a "Kid" cushion in accordance with the present invention.
Figure 23:
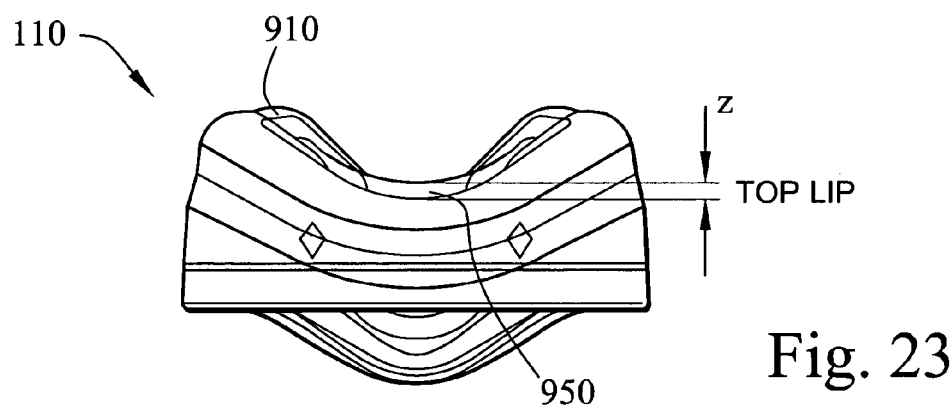
FIG. 23 illustrates a bottom view of a "Kid" cushion in accordance with the present invention, in comparison to the VISTA™ and/or other earlier embodiments.
Figure 37:
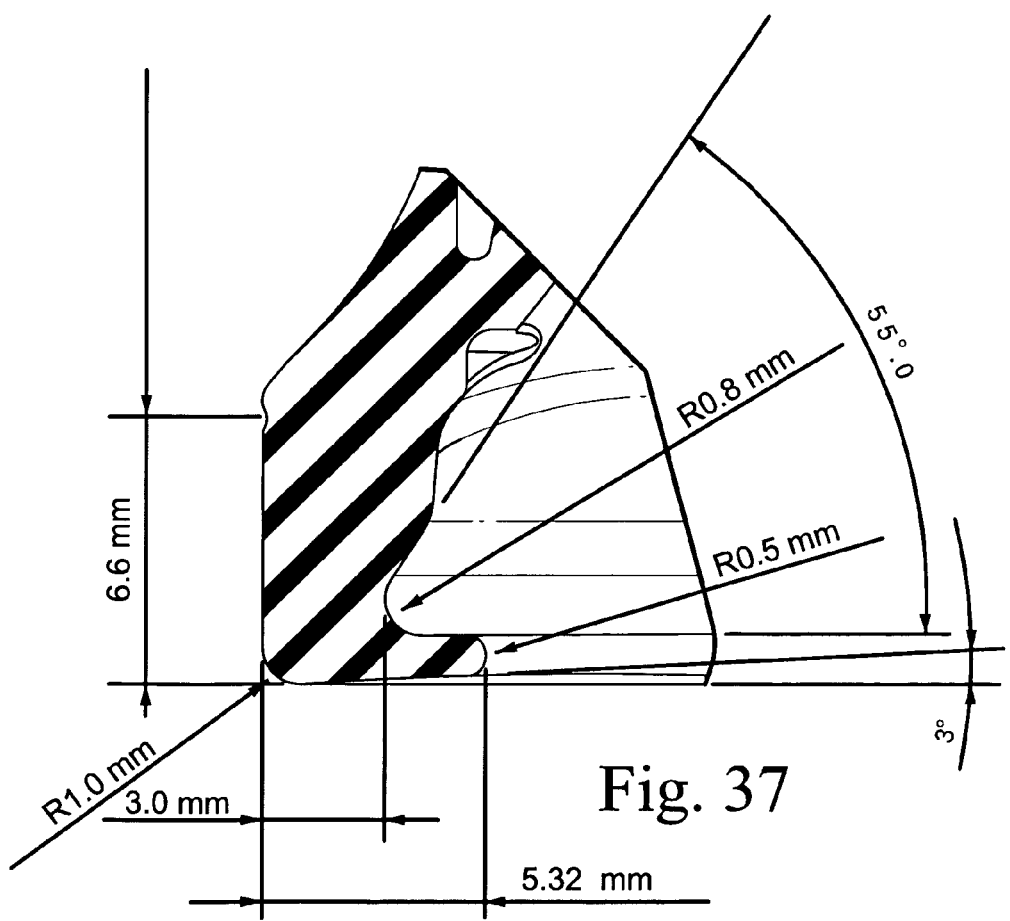
FIG. 37 is another detail view taken from FIG. 35.

The underlying rim 920 should preferably have the same cross section as the VISTA™, e.g., where it attaches to the frame as shown in FIG. 37, while the cross section of the membrane 910 and/or its relationship with the underlying rim 920 should be very similar to the VISTA™, bearing in mind that both should be tweaked at the nasal bridge area 930—the membrane 910 in particular. The cushion height (e.g., the distance measured from the underlying rim 920 (i.e., the upper lip (below the nose) to the top of the cushion as shown in FIG. 22) should be maintained if at all possible the same as the height of the VISTA™, keeping in mind that the height may be affected by having to fit the cushion 110 onto the frame 120.

As to the underlying rim 920, one aspect is to reduce the size of the opening 985 substantially along an entire extent thereof so that the width and effective height dimensions correspond to Table 6, all dimensions being in mm. For example, the width of the Kidsta S and XS may be in the range of about 30-42 mm, the effective height may be in the range of about 32-42 mm, and the effective bridge depth may be about 13-24 mm, although other dimensions are also possible. See FIG. 22, which shows the width and height of opening 985. The membrane 910 size follows the underlying rim 920 if proportions are maintained.

TABLE 6

VISTA ™, Kidsta S + Kidsta XS – Cushion

| | Width | Eff. Height | Bridge Depth |
|---|---|---|---|
| VISTA ™ | 45 | about 30 | <11 |
| KIDSTA—S | 39-40 | about 35 | <15 |
| KIDSTA-XS | 34-35 | about 40 | 20 |

Figure 24:
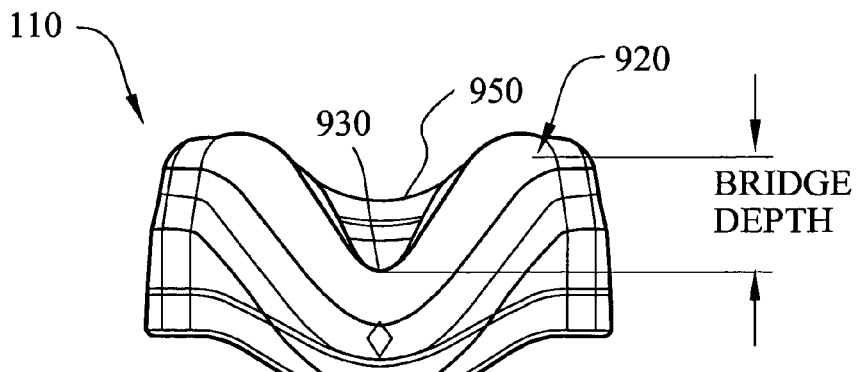
FIG. 24 illustrates a top view of a "Kid" cushion in accordance with the present invention.

The top lip 950 area should be raised so that a distance z is about 2 mm. See FIG. 23. The membrane bridge 930 should have an effective depth (i.e., the distance from the underlying rim 920 to the bottom of the nasal bridge region of the membrane 910, as shown in FIG. 24) that is preferably adjusted as shown in Table 6. See FIG. 24. The underlying rim 920 may be raised too if this helps with seating to frame 120. It may be desirable to adjust only the vertical dimension, although additional adjustment may be desirable.

Figure 25:
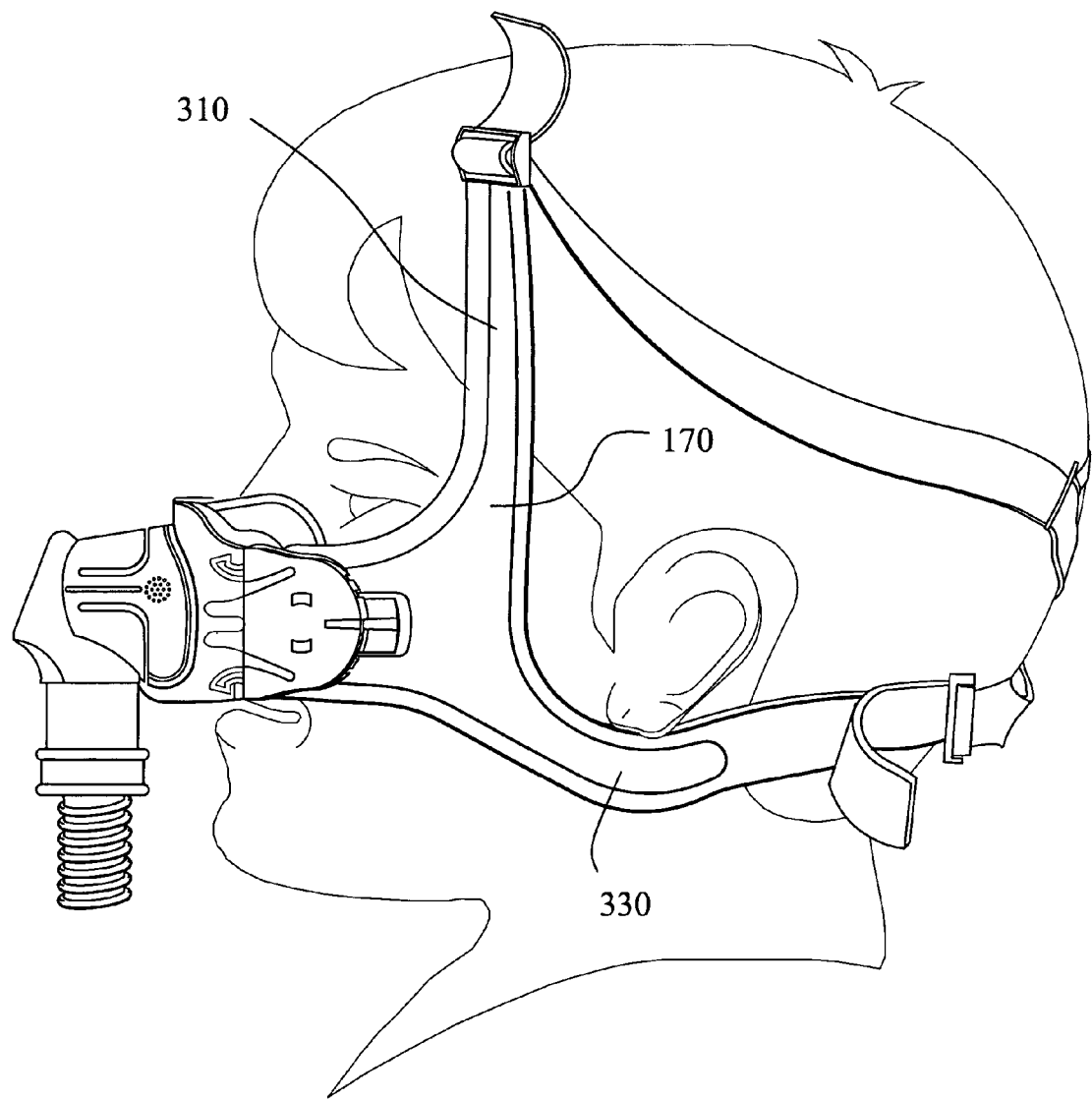
FIG. 25 illustrates a side view of a "Kid" cushion in use, in accordance with the present invention.
Figure 26:
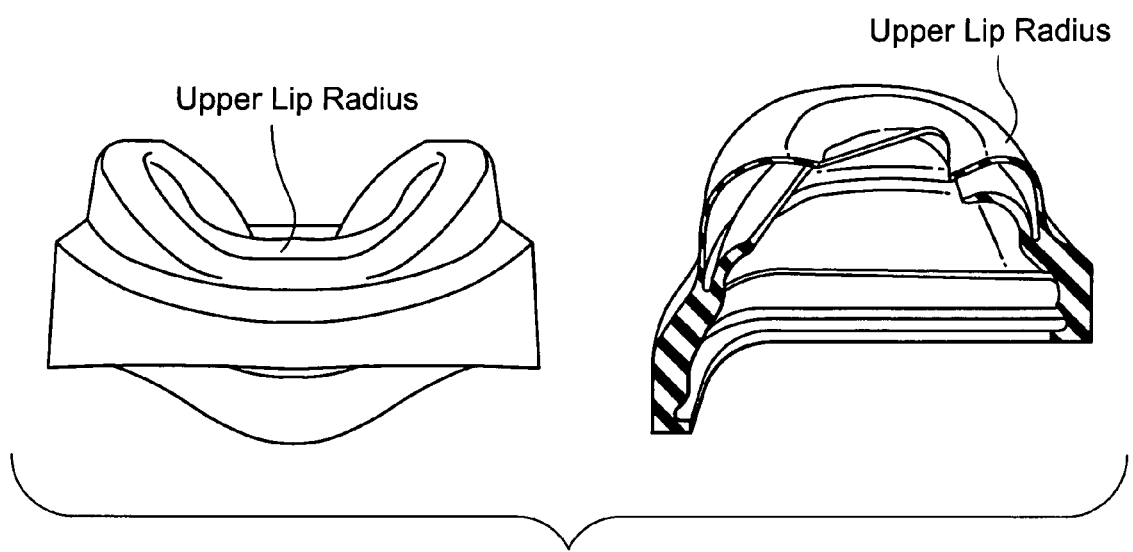
FIG. 26 illustrates features of the upper lip design for a cushion according to an embodiment of the present invention.

FIG. 25 shows a side view of the "Mini" or "Kid" described above, in use on a pre-adult. As shown, the vertical finger 310 of the yoke 170 may be too close to the user's eyes, and/or the yoke lower finger 330 may impinge on the lower part of the ear lobe. Accordingly, for the Kidsta-S, the dimension "C" from Table 4 can be increased by about 9 mm (i.e., a total of about 37 mm) to move the vertical finger closer to the ear, thereby increasing field of view. To better avoid or help avoid impinging on the lower ear lobe, dimensions "B" and/or "D" from FIG. 6 can be altered, for example, by increasing these dimensions by about 4 mm each, i.e., total dimension "B" would be about 90 mm and total dimension "D" would be about 50 mm (or a bit less than the VISTA™). The lower finger 330 may include a full radius.

The "Kid" or "Mini" can also be better dimensioned and/or shaped to avoid leak at the nasal bridge region, especially for kids under age 11 years old, to avoid intrusion into the eyes, to avoid discomfort stemming from a "hard-edged" cushion, and/or to reduce the size of the cushion, e.g., to avoid dead air space.

To better avoid intrusion into the eyes, the Kidsta XS cushion can be further shortened (compared to the Kidsta S) by about 5 mm to avoid the eye sockets. As mentioned, the frame size preferably remains the same.

The Kid or Mini cushion depth was about 3 mm deeper than the VISTA™, which may introduce possible instability and make headgear difficult to fit. In the Kidsta S, the height is reduced approximately to the height of the VISTA™.

In the Kid or Mini, the radius was smaller across the top lip (compared to the VISTA™) with no leaks or discomfort reported. Thus for the Kidsta S according to the present embodiment, maintain the 2 mm smaller radius compared to the VISTA™. For the Kidsta XS, the radius should be further reduced another 2 mm, in proportion, which may help accommodate patients with smaller lips. See FIG. 26.

As for sizing strategy, one aim is to use only 2 sizes with roughly equal population coverage. The dimensions which have the most impact on sizing are the maximum nose width (limits mask width), the minimum nose height from septum to eye line (limits mask height) and the minimum nasal bridge depth (limits shallowness of the mask). The inventors have found that width and height growth is approximately linear for the 5-16 age group. The masks are designed to fix approximately 5 year age blocks, and to fit the largest width and smallest height within each block. The data from the middle of the nasal bridge region is not widely available, so it is also assumed to be linear within each block. See Table 7, below.

TABLE 7

|  | Inner Cushion (Nose) Width | Inner Cushion (Nose) Height | Bridge Depth Difference c.t. Vista |
| --- | --- | --- | --- |
| VISTA ™ Standard | 45 | 40 | 0 |
| Kid or Mini | 40 | 36 | 5.5 |
| Kidsta Small | 40 | 35 | 8.5 |
| Kidsta Extra Small | 35 | 30 | 12.5 |

Figure 27:
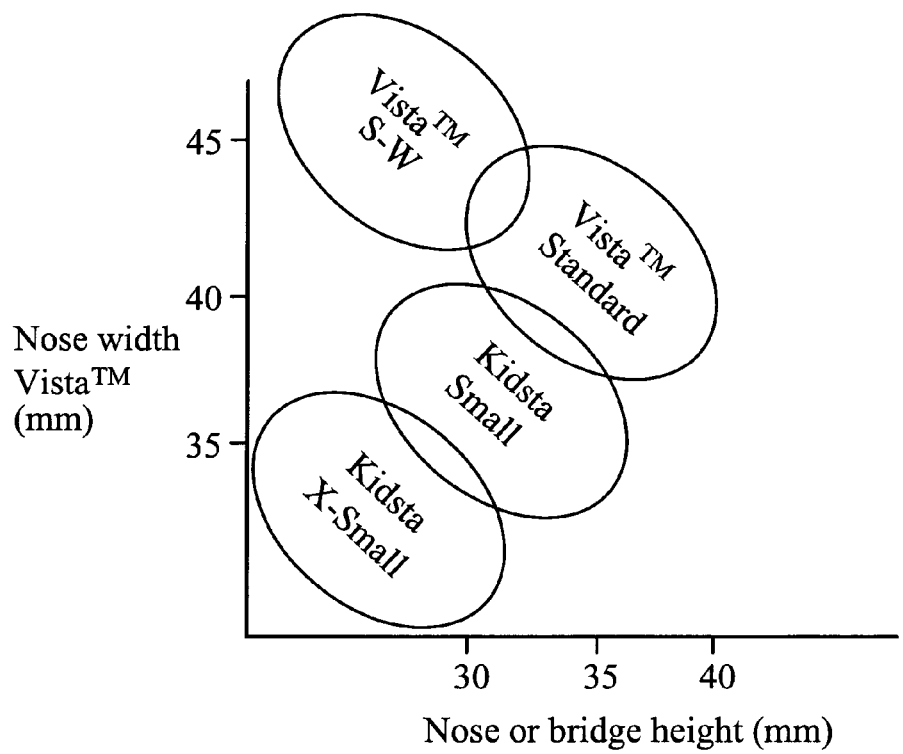
FIG. 27 illustrates a sample fitting chart plotting nose width v. nose or bridge height in accordance with the present invention, comparing the VISTA™, the Kidsta Small and the Kidsta Extra Small.

FIG. 27 is a sizing chart based on nose width and nose or bridge height. In accordance with an aspect of the invention, a mask (e.g., the Kidsta Small or the Kidsta XS) can be selected for a patient by measuring or otherwise obtaining one or more nose dimensions. For example, a Kidsta S or XS would be selected for a pre-adult or small sized adult patient having a nose width of less than about 40 mm and/or a nose/bridge height of less than about 35 mm. The Kidsta S and XS include cushions and/or headgear that are structured to provide a good fit for those patients. If the nose width is below about 35 mm and/or the nose/bridge height is below about 30 mm, then the Kidsta XS would appear to be the appropriate mask for that patient.

Figure 28:
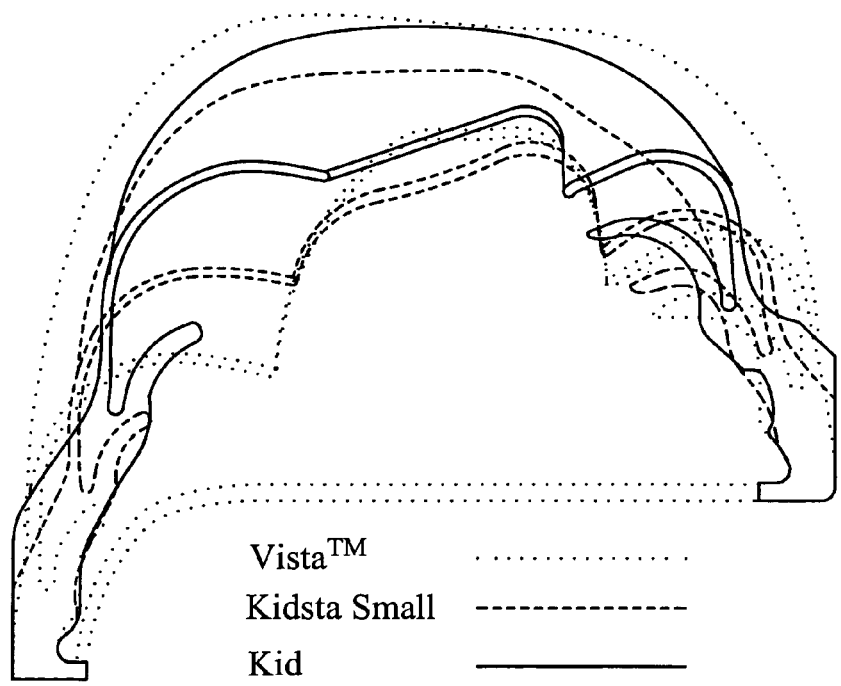
FIG. 28 illustrates cross-sectional views comparing the cushions of the "Kid", the Kidsta Small and the VISTA™.
Figure 29:
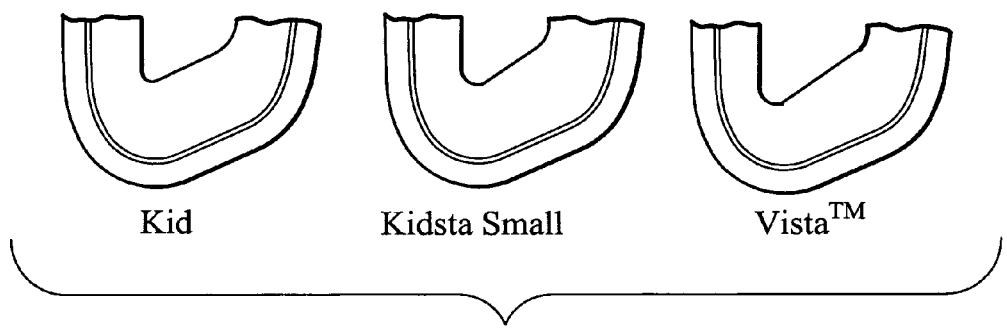
FIG. 29 illustrates partial plan views comparing the "Kid", Kidsta Small and VISTA™ cushions.

FIGS. 28-29 show various other features of the Kidsta S in conjunction with other cushions, for comparison purposes, VISTA™ and the Kid or Mini.

Figure 30:
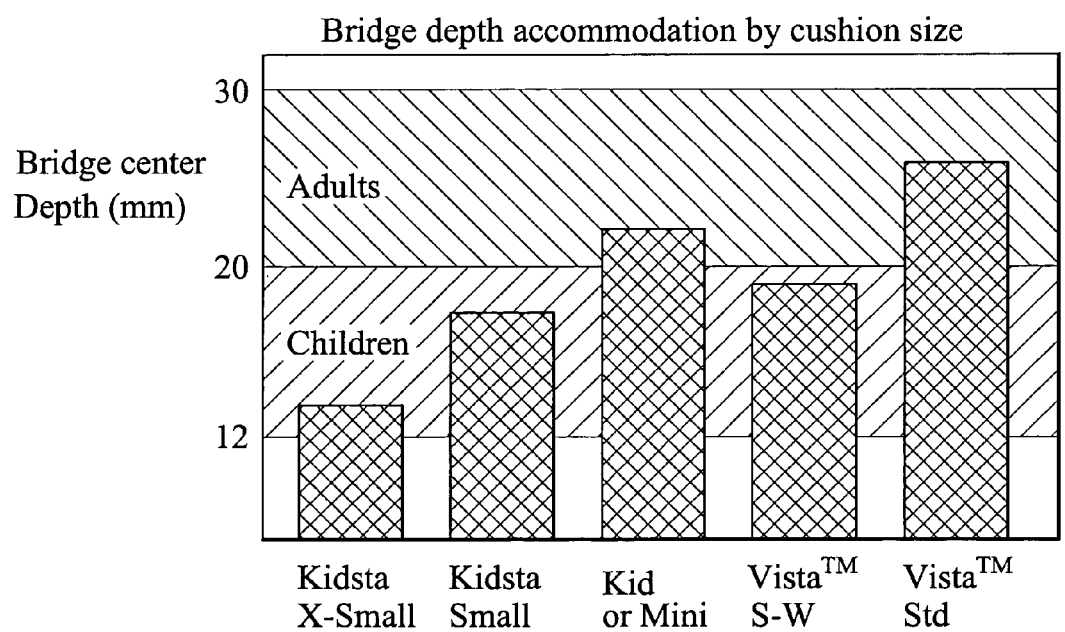
FIG. 30 illustrates a sample fitting chart based on bridge center depth, in accordance with an embodiment of the present invention.
Figure 31:
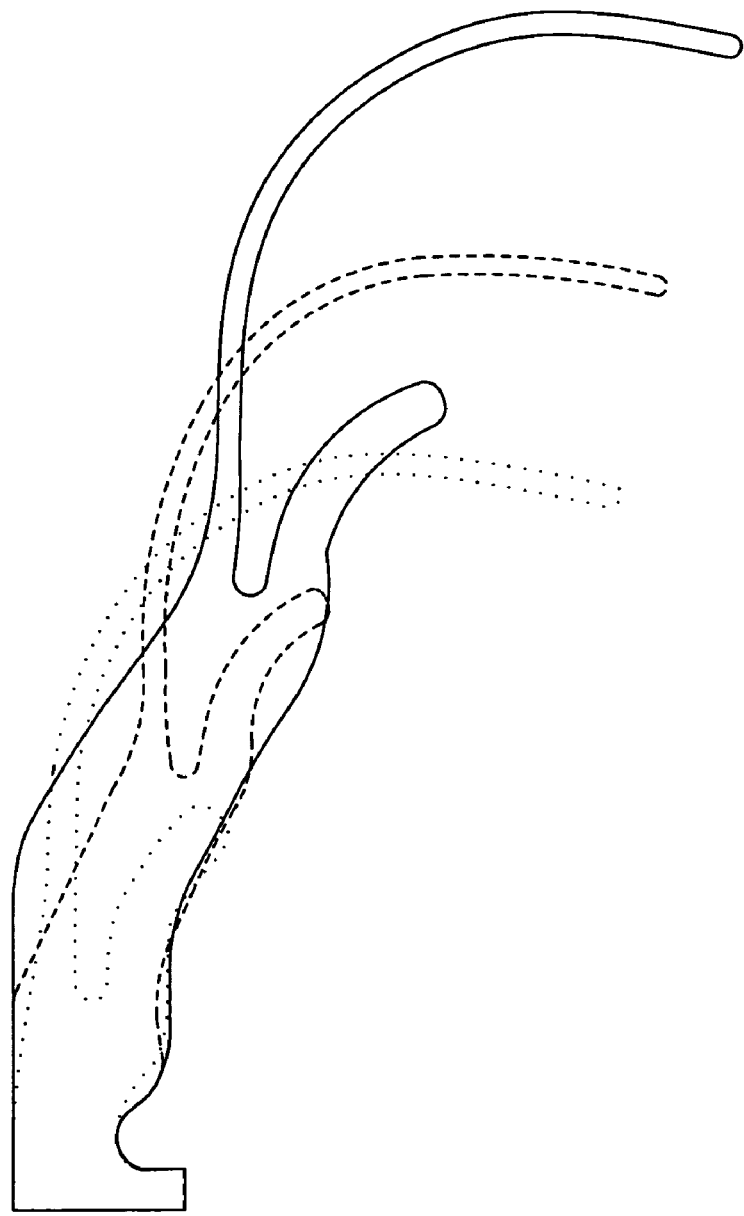
FIG. 31 illustrates partial cross-sectional views comparing the cushions of the "Kid", Kidsta Small and VISTA™.

FIG. 30 shows the bridge center depth versus cushion type, e.g., of the Kidsta S, Kidsta XS, the Kid or Mini, the VISTA™ (S-W) and the VISTA™ (Standard). The information in FIG. 30 can be combined with the information in FIG. 27 to select the most appropriate mask given one or more dimensions (and/or the age) of the patient. Compared to the Kid or Mini, the nasal bridge depth is reduced by about 3 mm for the Kidsta S, and 7 mm for the Kidsta XS. Also, the vent is the same as or similar to VISTA™. See FIG. 31.

FIGS. 32-37 show various views of the Kidsta S, while FIGS. 38-42 show various view of the Kidsta XS, including exemplary dimensions. The dimensions can be changed up to about ±20%, but preferably no more than up to about ±10%, of the exemplary values shown. FIGS. 32-42 are drawn to scale, or at least shown the relative distances between cushion parts to scale.

Figure 32:
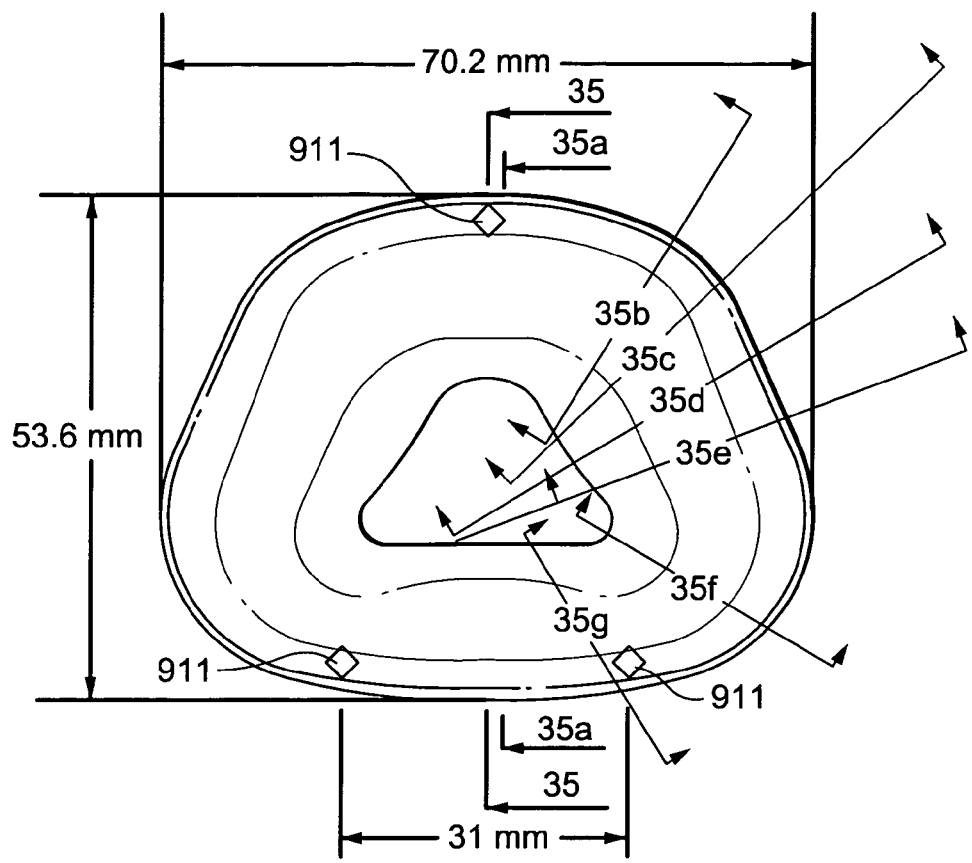
FIG. 32 illustrates a plan view of a Kidsta Small cushion in accordance with an embodiment of the present invention.
Figure 33:
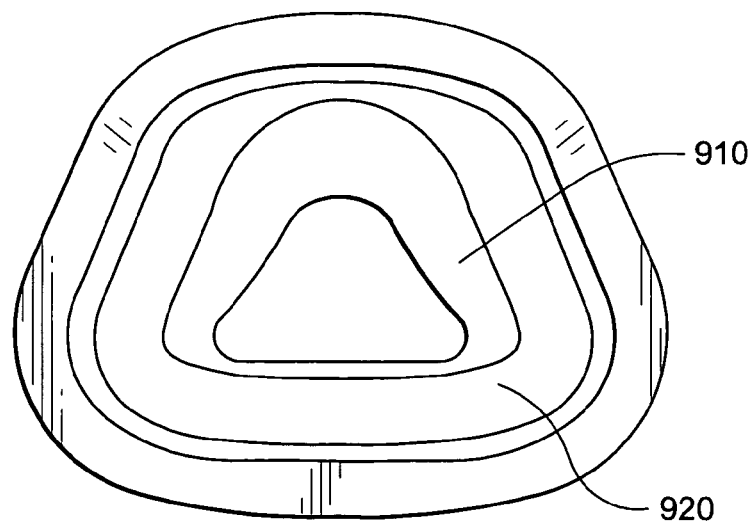
FIG. 33 is a rear view thereof.
Figure 34:
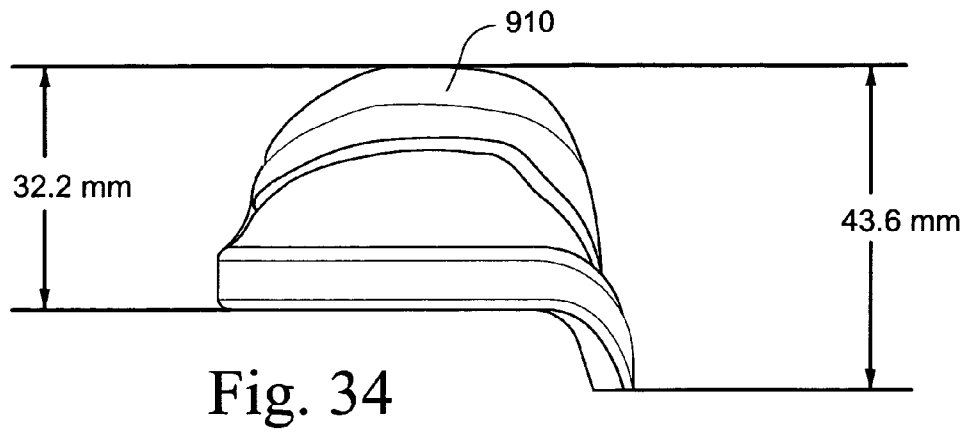
FIG. 34 is a side view thereof.
Figure 35:
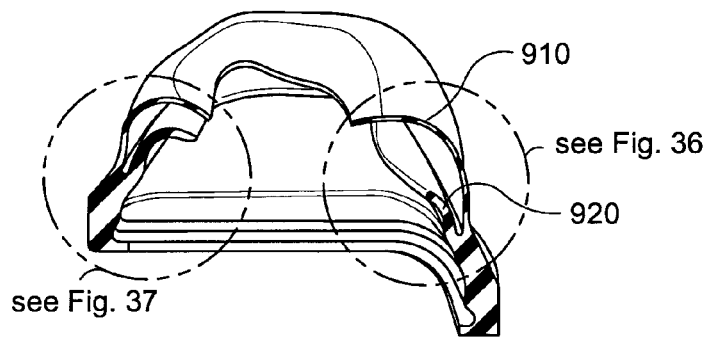
FIG. 35 is a cross-sectional view taken along section 35-35 in FIG. 32.
Figure 35A:
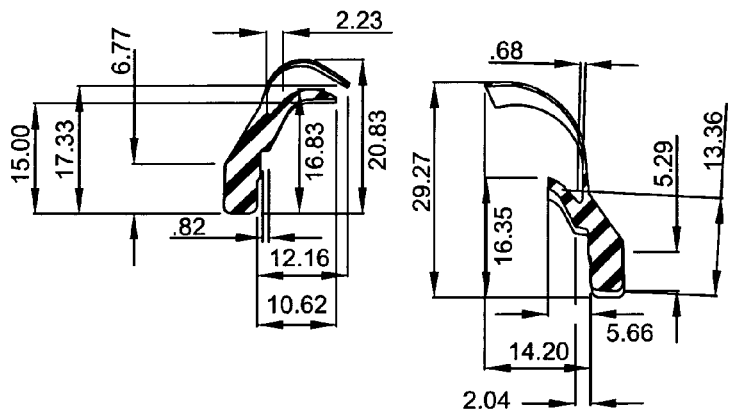
FIGS. 35a-35g illustrate exemplary cross-sections shown in FIG. 32, including dimensions and/or to-scale relative locations of the membrane relative to the rim.
Figure 35B:
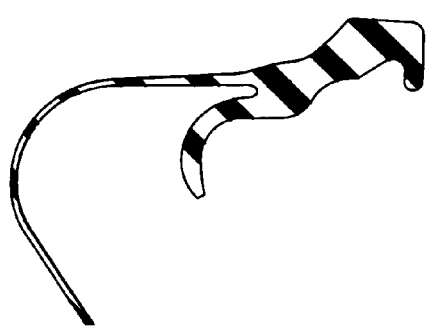
Figure 35C:
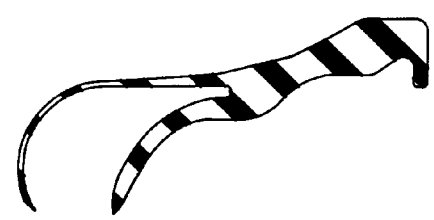
Figure 35D:
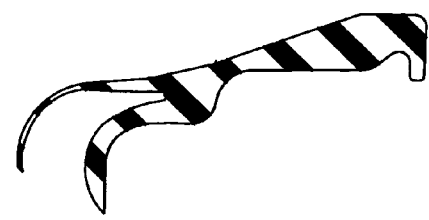
Figure 35E:
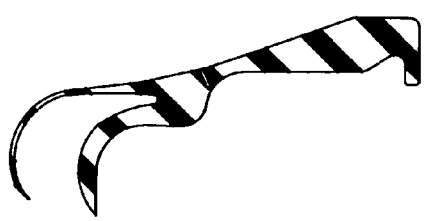
Figure 35F:
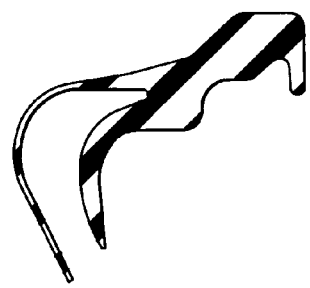
Figure 35G:
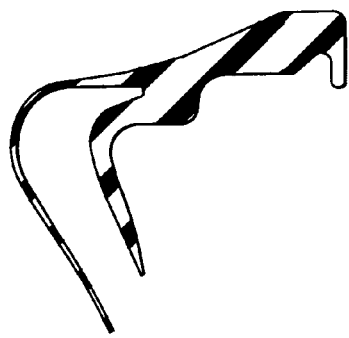
Figure 36:
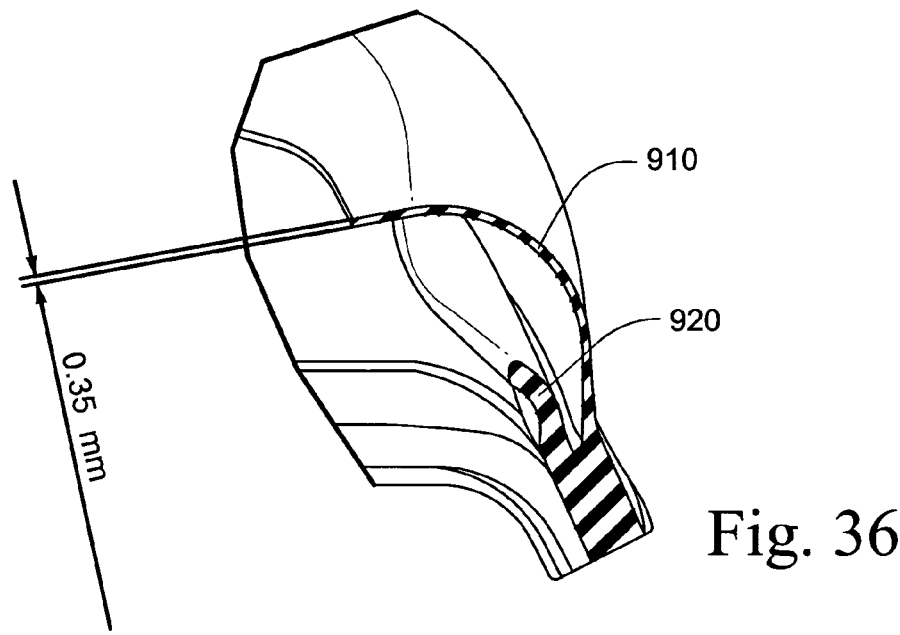
FIG. 36 is a detailed view taken from FIG. 35.
Figure 38:
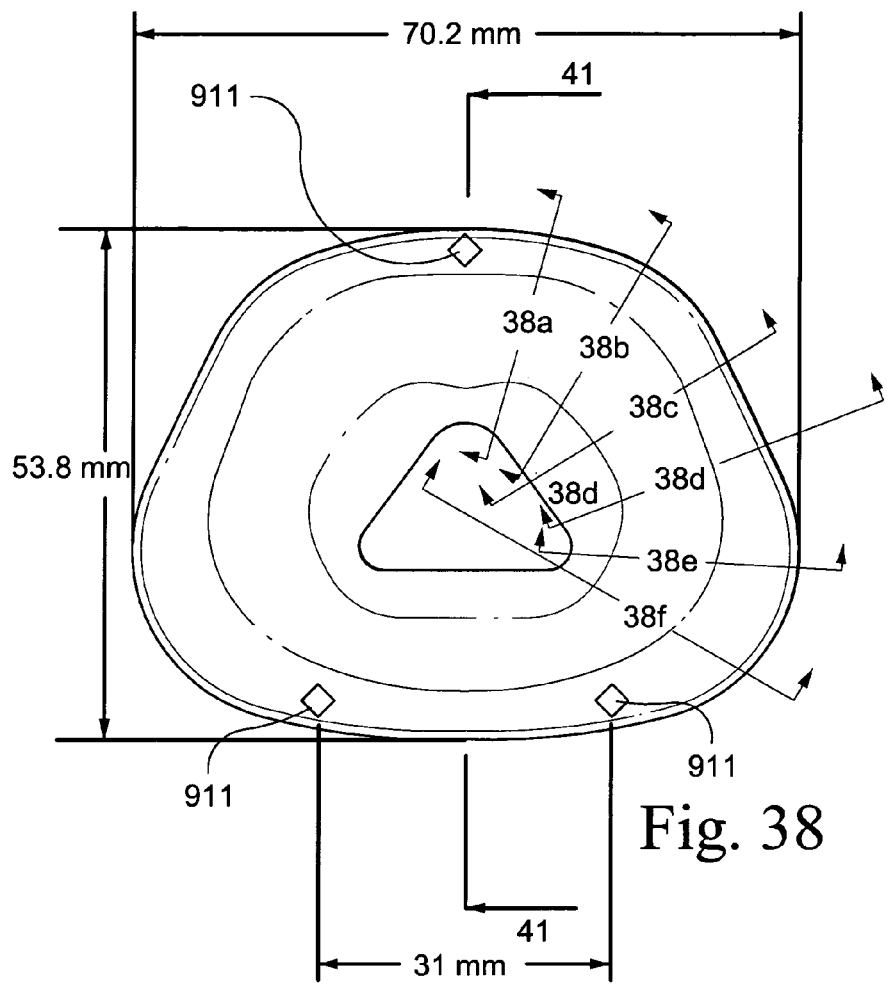
FIG. 38 illustrates a plan view of a Kidsta Extra Small cushion in accordance with an embodiment of the present invention.
Figure 39:
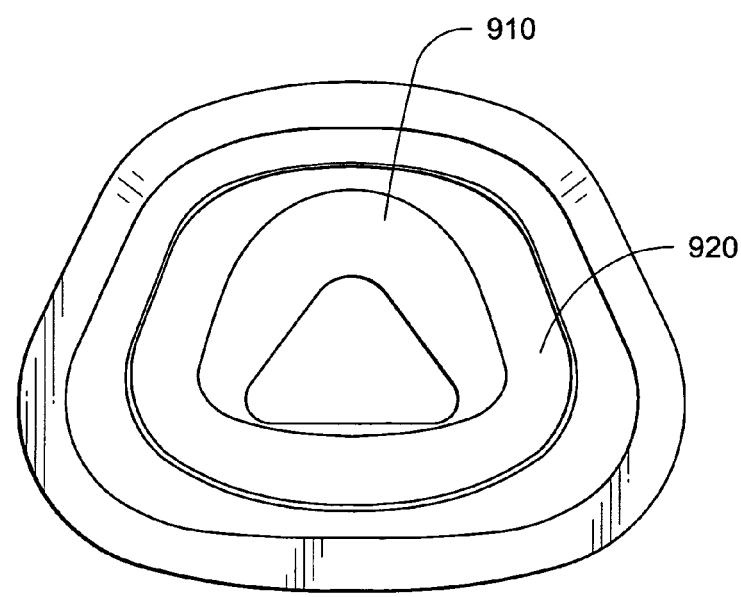
FIG. 39 is a rear view thereof.
Figure 40:
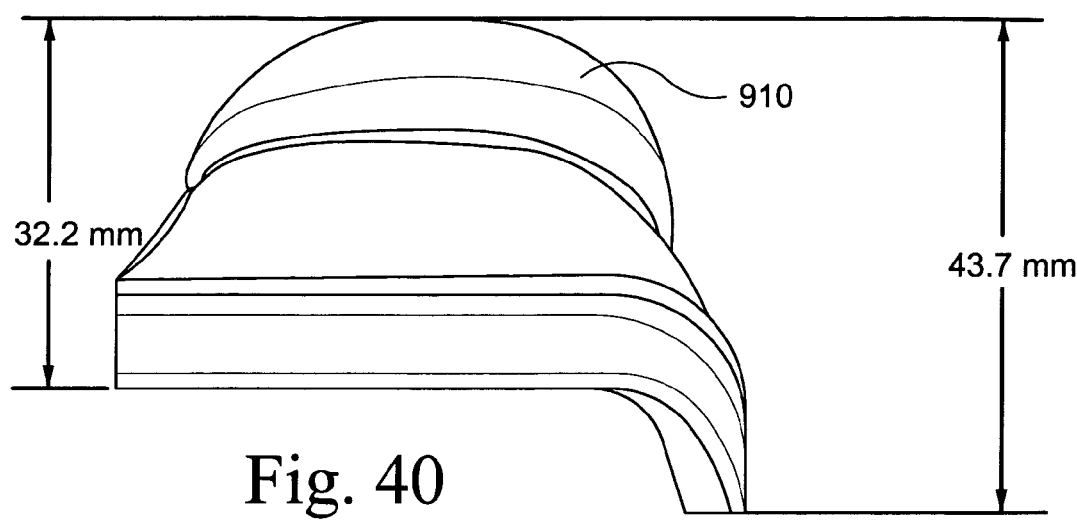
FIG. 40 is a side view thereof.
Figure 41:
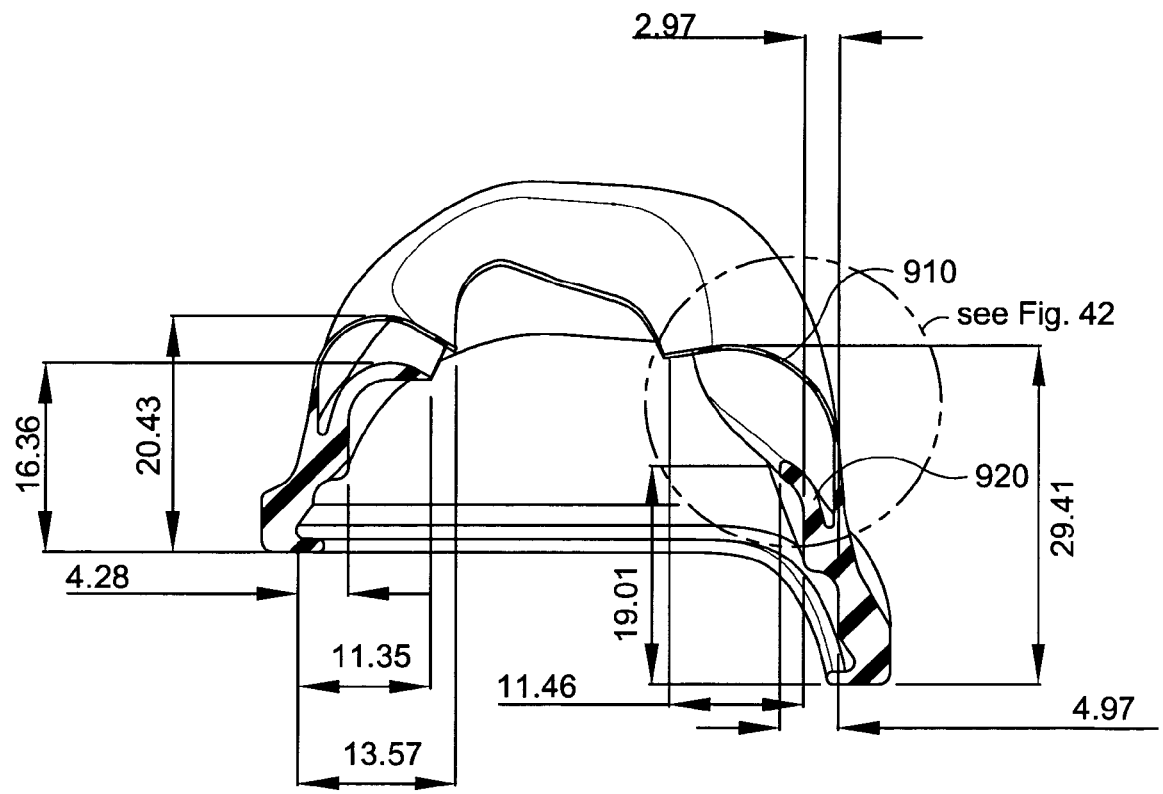
FIG. 41 is a cross-sectional view taken along section 41-41 of FIG. 38.
Figure 42:
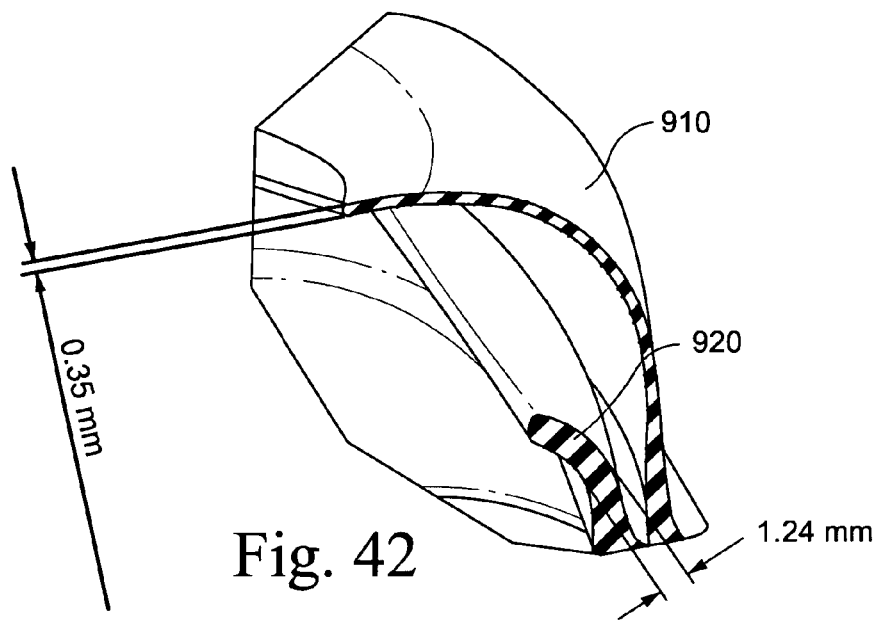
FIG. 42 is a detail view (scale:2 to 1) taken from FIG. 41.

As shown in FIGS. 32 and 38, the cushion may include one or more markers 911, e.g., in the form of a diamond or other shape. The markers may be provided in conjunction with similar or complimentary markings on the frame, to provide a visual indication to facilitate alignment.

Headgear Clip

The headgear clip 140 as shown in the VISTA™ (FIGS. 2-5) can be made of PBT, a plastic, resilient material, although other materials can be used. For the present embodiments, the clips can be made of polypropylene, preferably available under the trade name "BOREALIS." Clips made for polypropylene can be more flexible than PBT, which facilitates operation, e.g., assembly and disassembly, of the clip, especially by pre-adults, e.g., 5 year old girls can operate polypropylene clips. This can help increase compliance of the patient.

Frame

The existing VISTA™ type frame 120 includes cheek pieces (see FIGS. 2-5) that support the mask both vertically and from side to side movement. These cheek pieces preferably remain in light contact with the cheeks and/or jowls to provide the maximum stability with maximum comfort.

A problem may arise because different people have different face widths. A frame width that provides optimal contact for one person will be too tight for another person and too loose for a third.

If the frame is too tight, the patient may suffer from pain or skin damage, or will adjust the mask so that it is no longer too tight, but it will no longer seal or provide effective treatment. If the mask is too loose, the mask will have excessive side to side movement, especially when the patient turns to the side and presses one cheek into the pillow.

Another aspect of the invention is to chose a size that suits the largest number of patients, with a bias towards being too loose in preference to being too tight. It is envisaged that a range of sizes may be introduced so that customers may choose from a narrow, medium or wide mask frame.

Figure 43:
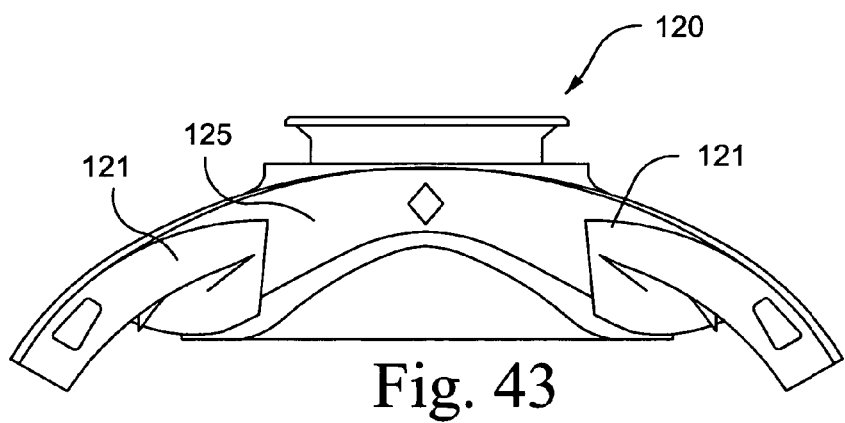
FIG. 43 is a top view of a frame in accordance with an embodiment of the present invention.
Figure 44:
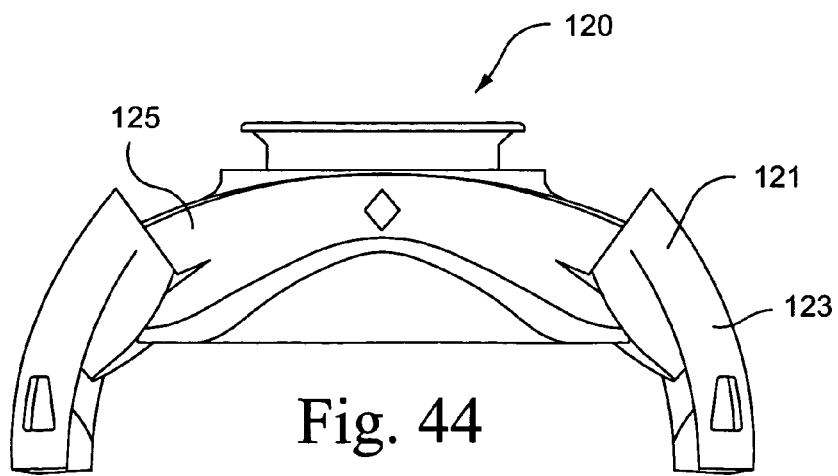
FIG. 44 shows the frame of FIG. 43 in a different position.

FIGS. 43-44 show a frame 120 having movable rather than rigid connections 121 between the cheek pieces 123 and the main body 125 of the mask frame. This enables the width of the frame between the cheek pieces to be adjusted to fit the patient.

There are a number of different ways that this idea can be implemented. For example, the cheek pieces 123 can be mounted on a hinge so that they can swing in or out. The cheek pieces 123 may be either free to move or they could be locked into one or more predetermined positions, via detents, friction, and/or a pin and slot arrangement.

Alternatively, the cheek pieces 123 can be flexibly mounted, so that they can bend in or out without requiring much force. If they are set so that the neutral position is wider than the patient's face, the tension in the headgear will pull the cheek pieces in towards the ideal position for that person.

In a further alternative, if the cheek pieces 123 are set so that the neutral position is narrower than the patient's face, the cheeks will push the cheek pieces out towards the ideal position for that person. In another method, the cheek pieces could be adjusted in or out using some sort of adjustment mechanism, such as a screw adjustment.

With movable cheek pieces, the mask can be more comfortable for a wider range of patients. Those patients with wide faces would no longer suffer from excessive pressure on the cheeks.

It would also be more securely mounted on the face, resulting in less mask movement for those with thin faces, or for people with wide faces who may adjust the mask poorly in an attempt to make it more comfortable. This greater security will result in less leakage, leading to greater comfort and more effective treatment.

This will make the VISTA™ type mask easier to fit onto a variety of different face shapes. Because one mask will fit such a large range, less inventory will be required.

Use of an adjustable mask frame will stop the need for having more than one frame size. This will reduce inventory and tooling costs.

The ease of fitting a wide variety of facial shapes will increase the range of people to whom the masks will be attractive. Although the invention has been described with reference to particular embodiments, it is to be understood that this embodiment is merely illustrative of the application of the principles of the invention. Numerous modifications may be made therein and other arrangements may be devised without departing from the spirit and scope of the invention.

What is claimed is:

1. Headgear for use with a respiratory mask, comprising:
   first and second straps each adapted to be provided to a mask frame of the mask, where each of the first and second straps includes a yoke, each said yoke being constructed and arranged to accommodate at least one of a pre-adult patient or a small sized adult patient, wherein:
   each said yoke includes a recess structure to allow connection between the frame and the yoke via a connector clip, each said yoke including a first dimension measured from the recess to a top portion of a yoke vertical finger, a second dimension measured from the recess to each end portion of a yoke horizontal finger, a third distance measured from the recess to a rear edge of the yoke vertical finger and a fourth distance measured from the recess to a lower edge of the lower finger; and
   the first distance is about 90-110 mm, the second distance is about 80-100 mm, the third distance is about 25-40 mm and the fourth distance is about 45-55 mm.

2. The headgear of claim 1, wherein the first distance is about 100 mm, the second distance is about 90 mm, the third distance is about 37 mm and the fourth distance is about 50 mm.

3. The headgear of claim 1, wherein the first and second straps are joined to one another at a rear portion of the patient's head in use via a cross-over member.

4. The headgear of claim 1, wherein the headgear includes a clip made of polypropylene.

5. A nasal mask having a relatively rigid mask frame and a relatively softer cushion provided to said frame, said cushion comprising:
   an outer membrane including a face-contact portion to form a seal with the patient;
   a frame connection portion opposite the face-contact portion;
   an inwardly sloping or stepped outer wall between the outer membrane and the frame connection portion; and
   an underlying rim positioned below the membrane,
   wherein the membrane and the rim are formed and positioned with respect to one another to accommodate at least one of a pre-adult patient or a small sized adult patient and the cushion includes a nasal bridge region, a top lip region and two side regions, and wherein a projected area of the frame connection portion is generally larger than an area defined by the face-contact portion of the membrane, wherein:
   the membrane and rim each have an orifice,
   a width of said membrane orifice is between about 30 and 32 mm in said lip region, between about 18 and 20 mm in each said side region, and between about 22 and 24 mm in said nasal bridge region,
   a width of the rim orifice is about 34 and 36 mm in the nasal bridge region, between about 32 and 34 mm in said lip region, and between about 42 and 44 mm in each said side region of the cushion,
   the membrane and the rim each have a height as measured from a portion of the cushion that engages the frame,
   the membrane height is about 27 and 35 mm in the nasal bridge region, between about 19 and 22 mm in the lip region, and between about 33-35 mm in each said side region,
   the rim height is between about 13 and 18 mm in the nasal bridge region and the lip region, and
   the rim height in each said side portion is between about 25 and 27 mm.

6. A nasal mask having a relatively rigid mask frame and a relatively softer cushion provided to said frame, said cushion comprising:
   an outer membrane including a face-contact portion to form a seal with the patient;
   a frame connection portion opposite the face-contact portion;
   an inwardly sloping or stepped outer wall between the outer membrane and the frame connection portion; and
   an underlying rim positioned below the membrane,
   wherein the membrane and the rim are formed and positioned with respect to one another to accommodate at least one of a pre-adult patient or a small sized adult patient and the cushion includes a nasal bridge region, a top lip region and two side regions, and wherein a projected area of the frame connection portion is generally larger than an area defined by the face-contact portion of the membrane, wherein the rim includes an aperture having a width of between about 30-42 mm, an effective height as vertically measured from an edge of the rim to a top of the cushion as seen in plan view of between about 32-42 mm, and an effective bridge depth of between about 13-24 mm as vertically measured from the membrane in the nasal bridge region to the rim in each said side region in top view.

7. The nasal mask of claim 6, wherein the width is between about 39-40 mm, the height is about 35 mm and the depth is less than about 15 mm.

8. The nasal mask of claim 6, wherein the width is about 34-35 mm, the height is about 40 mm and the depth is about 20 mm.

9. The nasal mask of claim 6, wherein the membrane generally follows a contour of the rim.

10. A nasal mask having a relatively rigid mask frame and a relatively softer cushion provided to said frame, said cushion comprising:
   an outer membrane including a face-contact portion to form a seal with the patient;
   a frame connection portion opposite the face-contact portion;
   an inwardly sloping or stepped outer wall between the outer membrane and the frame connection portion; and
   an underlying rim positioned below the membrane,
   wherein the membrane and the rim are formed and positioned with respect to one another to accommodate at least one of a pre-adult patient or a small sized adult patient and the cushion includes a nasal bridge region, a top lip region and two side regions, and wherein a projected area of the frame connection portion is generally larger than an area defined by the face-contact portion of the membrane wherein the membrane and the rim are formed and positioned with respect to one another to accommodate a pre-adult patient aged 16 years or less, wherein:
   the membrane and rim each have an orifice,
   a width of said membrane orifice is between about 30 and 32 mm in said lip region, between about 18 and 20 mm in each said side region, and between about 22 and 24 mm in said nasal bridge region, and
   a width of the rim orifice is about 34 and 36 mm in the nasal bridge region, between about 32 and 34 mm in said lip region, and between about 42 and 44 mm in each said side region of the cushion.

11. The nasal mask of claim 10, wherein the membrane and the rim each have a height as measured from a portion of the cushion that engages the frame,
   the membrane height is about 27 and 35 mm in the nasal bridge region, between about 19 and 22 mm in the lip region, and between about 33-35 mm in each said side region,
   the rim height is between about 13 and 18 mm in the nasal bridge region and the lip region, and
   the rim height in each said side portion is between about 25 and 27 mm.

12. A nasal mask having a relatively rigid mask frame and a relatively softer cushion provided to said frame, said cushion comprising:
   an outer membrane including a face-contact portion to form a seal with the patient;
   a frame connection portion opposite the face-contact portion;
   an inwardly sloping or stepped outer wall between the outer membrane and the frame connection portion; and
   an underlying rim positioned below the membrane,
   wherein the membrane and the rim are formed and positioned with respect to one another to accommodate at least one of a pre-adult patient or a small sized adult patient and the cushion includes a nasal bridge region, a top lip region and two side regions, and wherein a projected area of the frame connection portion is generally larger than an area defined by the face-contact portion of the membrane wherein the membrane and the rim are formed and positioned with respect to one another to accommodate a pre-adult patient aged 16 years or less, wherein the rim includes an aperture having a width of between about 30-42 mm, an effective height as vertically measured from an edge of the rim to a top of the cushion as seen in plan view of between about 32-42 mm, and an effective bridge depth of between about 13-24 mm as vertically measured from the membrane in the nasal bridge region to the rim in each said side region in top view.

13. The nasal mask of claim 12, wherein the width is between about 39-40 mm, the height is about 35 mm and the depth is less than about 15 mm.

14. The nasal mask of claim 13, wherein the width is about 34-35 mm, the height is about 40 mm and the depth is about 20 mm.

* * * * *